United States Patent [19]

Cate et al.

[11] Patent Number: 5,359,033

[45] Date of Patent: Oct. 25, 1994

[54] CLEAVED DIMERS OF MULLERIAN INHIBITING SUBSTANCE-LIKE POLYPEPTIDES

[75] Inventors: Richard L. Cate, Cambridge; R. Blake Pepinsky, Watertown, both of Mass.

[73] Assignee: Biogen, Inc., Cambridge, Mass.

[21] Appl. No.: 80,140

[22] PCT Filed: Jan. 25, 1989

[86] PCT No.: PCT/US89/00239

§ 371 Date: Jul. 23, 1990

§ 102(e) Date: Jul. 23, 1990

[87] PCT Pub. No.: WO89/06695

PCT Pub. Date: Jul. 27, 1989

Related U.S. Application Data

[63] Continuation of Ser. No. 543,719, Jul. 23, 1990, abandoned.

[51] Int. Cl.$^5$ .......... C12P 21/06; C12Q 1/00; C07K 3/00; C07K 15/00

[52] U.S. Cl. .......... 530/350; 435/69.1; 435/69.4; 530/300; 530/351

[58] Field of Search .......... 435/69.1, 69.4, 7.21, 435/7.23; 530/300, 350, 351; 514/2, 8, 12

[56] References Cited

U.S. PATENT DOCUMENTS 4,404,188 9/1983 Donahoe et al. .......... 530/350

Primary Examiner—Robert J. Hill, Jr.
Assistant Examiner—Gian P. Wang
Attorney, Agent, or Firm—James F. Haley, Jr.; Ivor R. Elrifi

[57] ABSTRACT

This invention relates to cleaved dimers of Mullerian inhibiting substance-like polypeptides. More particularly, this invention relates to such dimers, methods of producing them and methods of using them in the treatment of cancer and tumors, especially those of the female genital tract. The dimers of this invention are also useful in compositions and methods for contraception.

5 Claims, 18 Drawing Sheets

MIS 140K DIMER OF 70K SUBUNITS

PROTEASE OR PLASMIN

NON-COVALENT COMPLEX OF 110K AND 25K DIMERS

ACIDIFICATION, BOILING OR DEOXYCHOLATE

110K DIMER OF 57K SUBUNITS | 25K DIMER OF 12.5K SUBUNITS

```
  1 CAAGGTCATGTCCCAGGAGGAGATAGGGACCGCCCTGCACCACAAACAGCTCTGCTCCCTCTTATAAAGTAGGGCAGCCCAGCCCTGGAAGCTCCCAGG  100
    ----+----+----+----+----+----+----+----+----+----+----+----+----+----+----+----+----+----+----+----+
    GTTCCAGTATACAGGGTCCTCCTCTACTCTCTGCGGGACGTGGTGTTTGTCGAGACGAGGAGAATATTTCATCCCGTCGGGTCGGGGACCTTCGAGGGTCC

101 ATGCCCGGTCCATCTCTCTGGCCCTGGTGCTGTCGGCCATGGGGGCTCTGCTGAGGCCAGGGACCCCTGAGGGGACCTCCCTGGGGGTCCCTTCTTCAGAAGTCTTCAGCACCTCAGCCT  200
    ----+----+----+----+----+----+----+----+----+----+----+----+----+----+----+----+----+----+----+----+
    TACGGGCCAGGTAGAGAGACCGGGACCACGACAGCCGGTACCCCCGAGACGACTCCGGTCCCTGGGGACTCCCCTGGAGGGACCCCCAGGGAAGAAGTCTTCAGAAGTCGTGGAGTCGGA
    M  P  G  P  S  L  A  L  V  L  S  A  M  G  A  L  L  R  P  G  T  P ┌MATURE SEQUENCE
                                                                     R  E  E  V  F  S  T  S  A  L

201 TGCCCAGGGAGCAGGCCACAGGCGGGGCACTCATCTTTCAGCAAGCCTGGGACTGGCCACTCTCCAGTCTCTGGCTGCCAGGCAGCCCTCTGGACCC  300
    ----+----+----+----+----+----+----+----+----+----+----+----+----+----+----+----+----+----+----+----+
    ACGGGTCCCTCGTCCGGTGTCCGCCCCGTGAGTAGAAAGTCGTTCGGACCCTGACCGGTGAGAGACCGACGGTCAGAGACCGACGGTCCGTCGGGAGACCTGGG
    P  R  E  Q  A  T  G  S  G  A  L  I  F  Q  Q  A  W  D  W  P  L  S  S  L  W  L  P  G  S  P  L  D  P

301 CCTGTGCCTGGTGACCCTGCATGGGAGTGGCCGGGGGGAGCAGGCCTTCCTGGAGGCT  400
    ----+----+----+----+----+----+----+----+----+----+----+----+----+----+----+----+----+----+----+----+
    GGACACGGACCACTGGGACGTACCCTCACCGGCCCCCCCTCGTCCGGAAGGACCTCCGA
    P  L  C  L  V  T  L  H  G  S  G  N  G  S  R  A  P  L  R  V  V  G  V  L  S  S  Y  E  Q  A  F  L  E  A

401 GTGCGGCGACACCCACTGGGGCCTGAGTGACTTGACCACCTTCGCAGTGTGCCCCGGCTGTGCCCCACCCTTGCTGAGGTTCCAGGAGCCTGCAG  500
    ----+----+----+----+----+----+----+----+----+----+----+----+----+----+----+----+----+----+----+----+
    CACGCCGCTGTGGGTGACCCCGGACTCACTGAACTGGTGGAAGCGTCACACGGGGTCACACGGGGTGGGAACGACTCCAAGGTCCTCGGACGTC
    V  R  T  H  W  G  L  S  D  L  T  T  F  A  V  C  P  A  G  N  G  Q  P  V  L  P  H  L  Q  R  L  Q  A

501 CATGGCTGGGGGAGCCCGGGGGGCCCCCGGGCCCCTCGGGGTGACTGAACTGGTGGAACCTGGACCTGGTTCACACTGAACGACGTGCACCGCGTC  600
    ----+----+----+----+----+----+----+----+----+----+----+----+----+----+----+----+----+----+----+----+
    GTACCGACCCCCTCGGGCCCCCCGGGGGCCCGGGGAGCCCCACTGACTTGACCACCTTGGACCTGGAACCAAGTGTGACTTGCTGCACGTGGCGCAG
    W  L  E  E  V  T  W  E  P  T  P  L  L  R  F  Q  E  P  P  P

601 TGGAGGAGCCAGCCCCAGCCCCCAGAGCTGGCGCTGCTGGTGGTGTACCCAGGGCCTGGTGTAACCGTGACCGGAGCGGG  700
    ----+----+----+----+----+----+----+----+----+----+----+----+----+----+----+----+----+----+----+----+
    ACCTCCTCGGTCGGGGTCGGGGGTCTCGACCGCGACGACCACCACATGGGTCCCGGACCACATTGGCACTGGCCTCTCG
    G  G  A  S  P  P  E  L  A  L  L  V  V  Y  P  G  P  G  L  E  V  T  V  T  G  A  G  L  P  G  T  Q  S
```

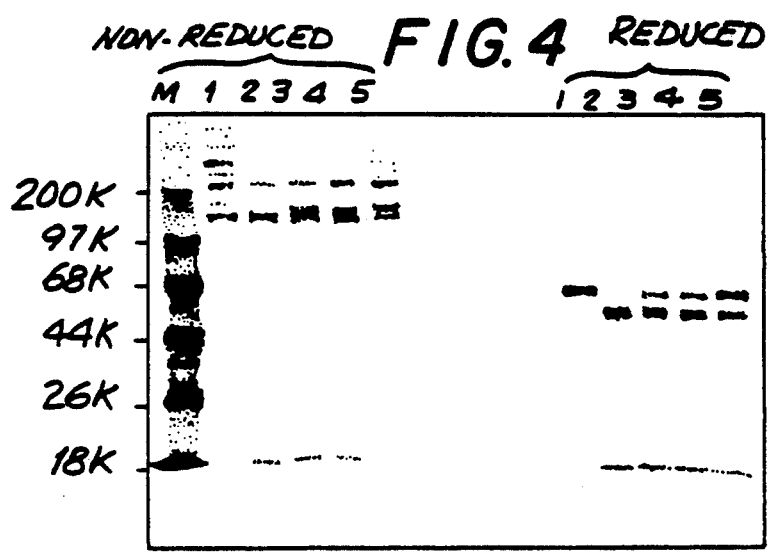
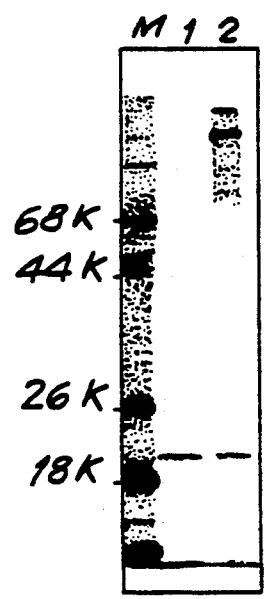

Sequence of MIS100 probe
    CGGTGGCCCC CGGCTAGCGC TGTGCCCGAC

Sequence of MIS103 probe
    GATCCTCGAG GACCAGGTCG TGCTCAGACG TCTGCTGGGG

Sequence of MIS104 probe
    CCACTGCGGC CGATGGTCCA TGTGCACTGC GTGAGCT

Sequence of MIS105 probe
    CAGTGGCCCC AGCAGACGTC TGAGCACGAC CTGGTCCTCG AG

Sequence of MIS106 probe
    CACGCAGTGC ACATGGACCA TCGGCCG

*FIG. 8*

CLEAVED DIMERS OF MULLERIAN INHIBITING SUBSTANCE-LIKE POLYPEPTIDES

This application is a continuation of application Ser. No. 07/543,719, filed Jul. 23, 1990, now abandoned

TECHNICAL FIELD OF INVENTION

This invention relates to cleaved dimers of Mullerian inhibiting substance-like polypeptides. More particularly, this invention relates to such dimers, methods of producing them and methods of using them in the treatment of cancer and tumors, especially those of the female genital tract. The dimers of this invention are also useful in compositions and methods for contraception.

BACKGROUND OF THE INVENTION

Mullerian Inhibiting Substance (MIS) is a glycoprotein produced by the Sertoli cells of the embryonic testis. It is a non-steroidal factor that causes regression of the Mullerian duct, the anlagen of the internal female reproductive tract [Jost, *Rec. Prog. Horm. Res.*, 8, 379–418 (1953)]. MIS, in addition to its important role in development, has been shown to be cytotoxic to the human ovarian tumor cell line HOC-21, both in vitro and in vivo (in a nude mouse model) [Donahoe et al., *Science*, 205, 913–15 (1979); Fuller et al., *J. Clin. Endocrinol. Metab.*, 54, 1051–55 (1982); Donahoe et al., *Ann. Surg.*, 194, 472–80 (1981)].

Both human MIS and bovine MIS have been cloned and expressed in various bacterial and animal host cells using both genomic and cDNA sequences. The products of such recombinant transformed cells, as well as those of Sertoli cells, are 70K polypeptides which dimerize to form 140K disulfide-linked dimers. The purified dimers from Sertoli cells or recombinant cells (e.g., CHO cells transfected with an MIS gene) are active in vitro in causing regression of the rat Mullerian duct in a standard organ culture assay [Cate et al., *Cell*, 45, pp. 685–98 (1986)].

SUMMARY OF THE INVENTION

The present invention relates to dimers of MIS-like polypeptides (bovine, human or other mammal) which may be processed to produce a C-terminal dimer and a N-terminal dimer. These dimers may remain non-covalently associated with each other and are active in a standard organ culture assay for biological activity of an MIS protein [Cate et al., supra]. The associated dimers, which may also be separated from each other by boiling, acidification or treatment with a detergent such as deoxycholate, are useful separately or in combination in the treatment of cancer, especially cancer of the female genital tract. The dimers of this invention are also useful in compositions and methods for contraception.

BRIEF DESCRIPTION OF THE DRAWINGS

FIG. 2 depicts the genomic DNA of a human MIS. It also depicts the amino acid sequence of immature and mature human MIS—those sequences are interrupted by four introns at the DNA level. In this figure, the amino acids are represented by single letter codes as follows:

| Phe: F | Leu: L | Ile: I | Met: M |
| Val: V | Ser: S | Pro: P | Thr: T |
| Ala: A | Tyr: Y | His: H | Gln: Q |
| Asn: N | Lys: K | Asp: D | Glu: E |
| Cys: C | Trp: W | Arg: R | Gly: G |

Figure 3B:
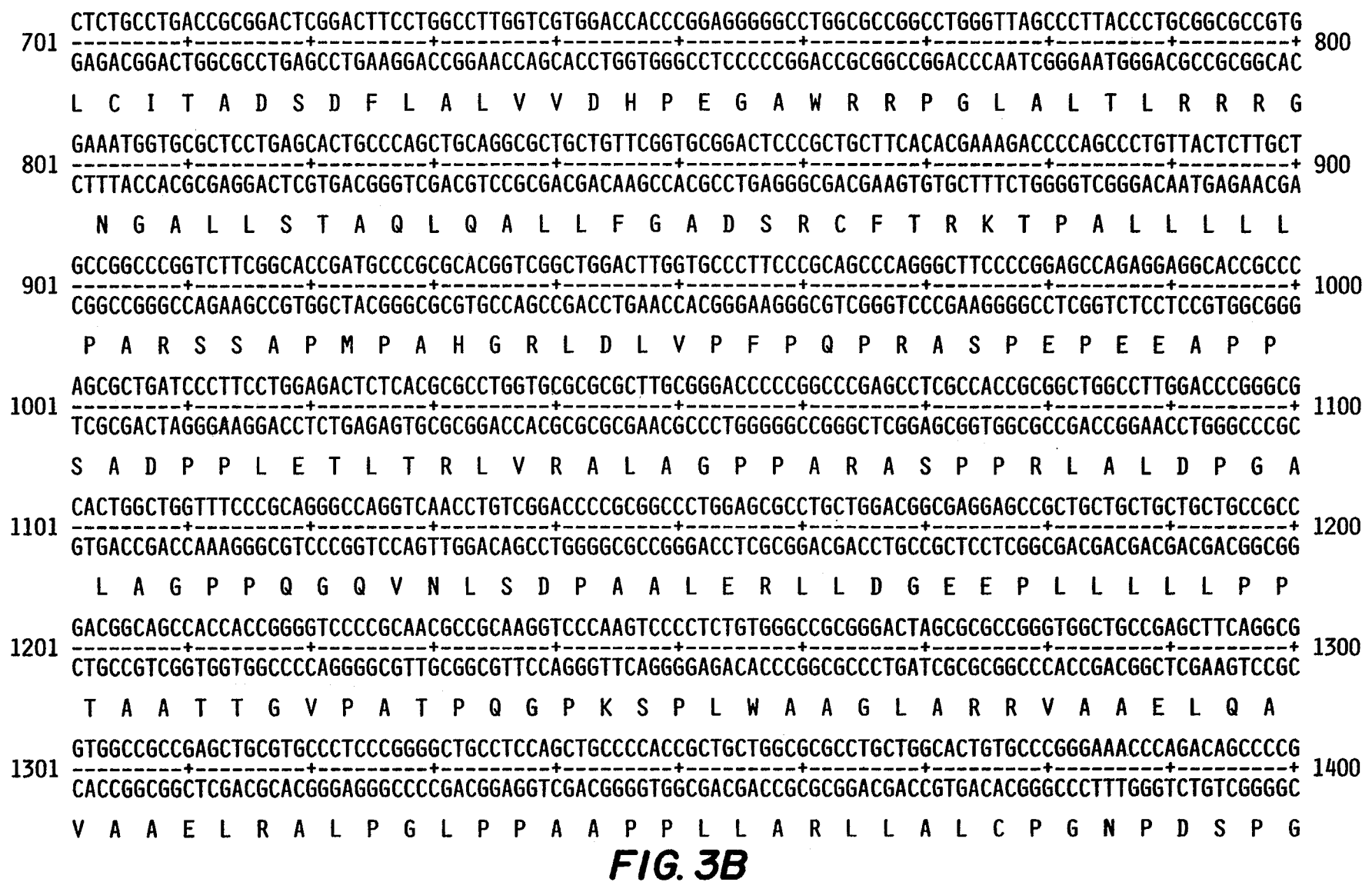
Figure 3C:
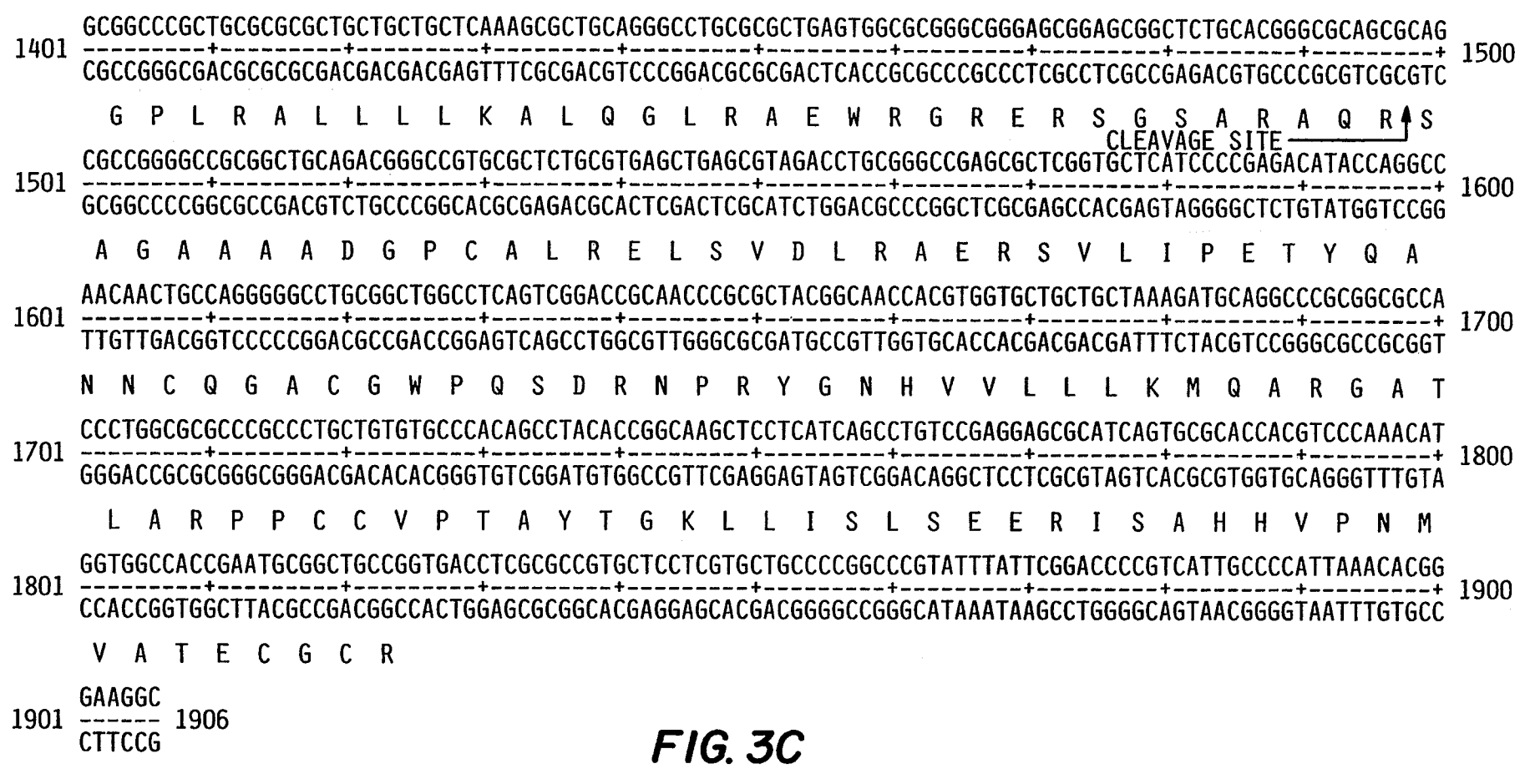

FIG. 3 depicts the DNA and amino acid sequences of immature and mature bovine MIS. It is a genomic/cDNA composite sequence.

FIG. 4 is a SDS-PAGE of plasmin digested MIS which shows that plasmin cleavage of MIS produces an N-terminal (110 kDa) and C-terminal (25 kDa) dimer.

FIG. 5 is a SDS-PAGE which shows that deoxycholate dissociates the non-covalent complex between the N- and C-terminal dimers.

Figure 6:
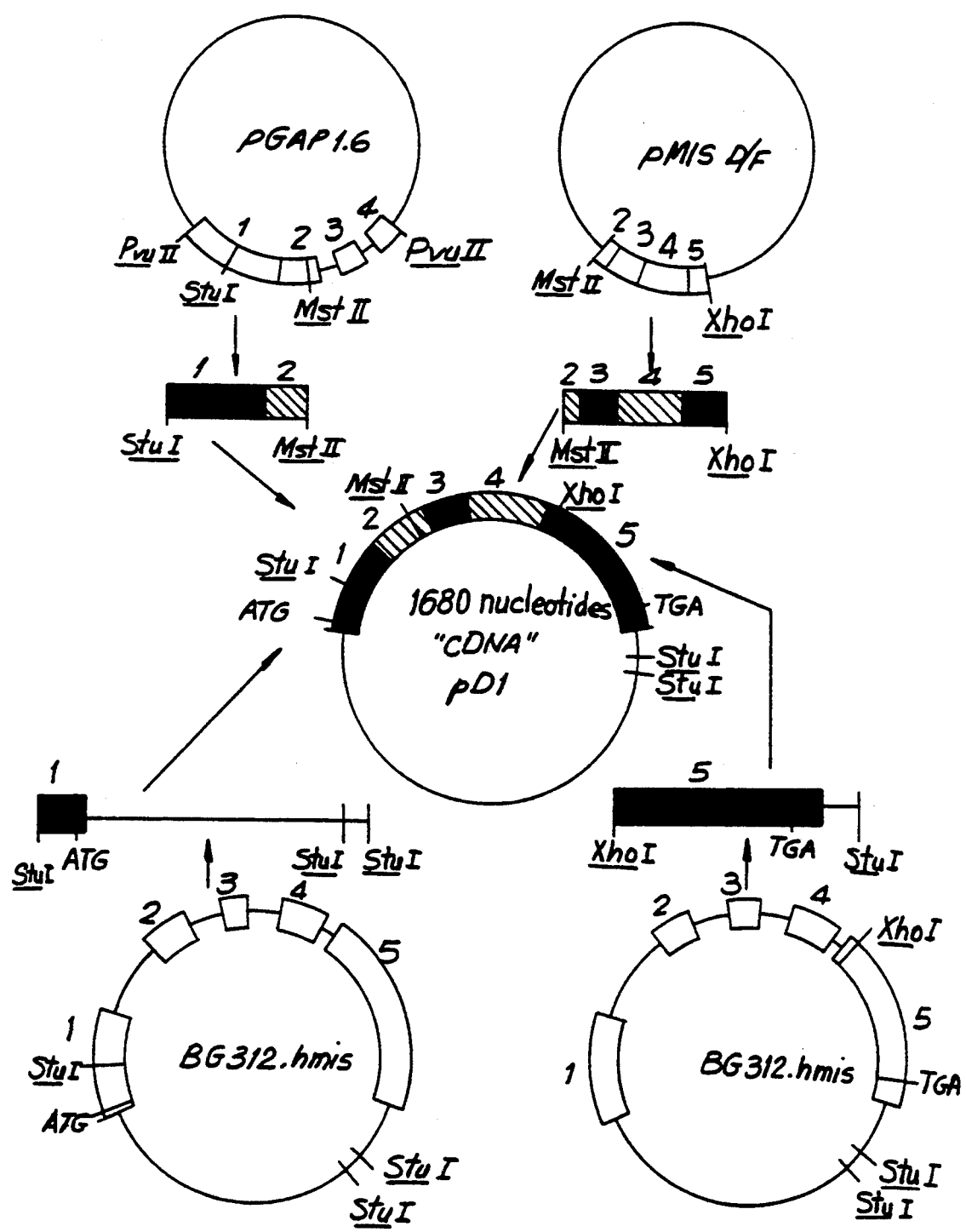

FIG. 6 is a schematic outline of the construction of plasmid pD1.

FIGS. 7A–7D are schematic outlines of the construction of plasmid pJ103.

FIG. 8 depicts the nucleotide sequence of oligomers MIS100, MIS103, MIS104, MIS105, MIS106.

Figure 9:
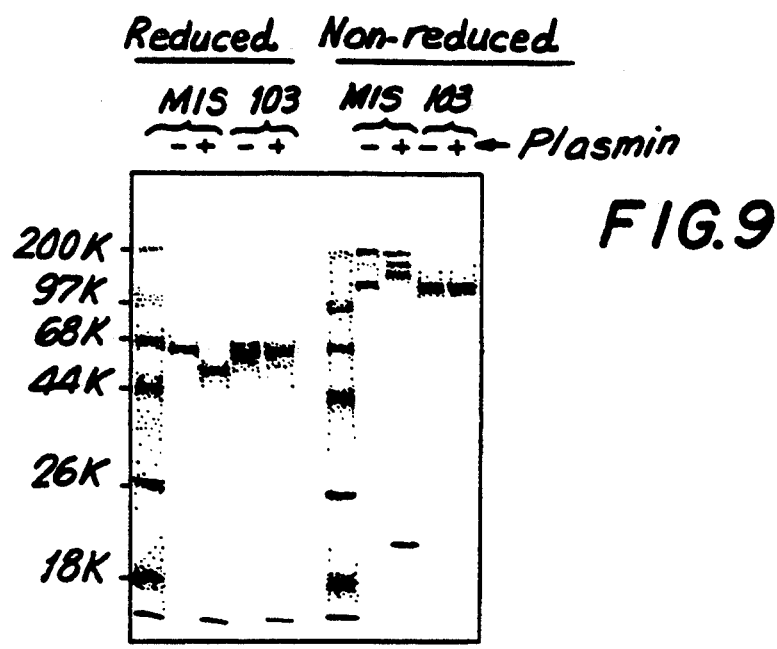

FIG. 9 is a SDS-PAGE analysis of purified mutant 103 produced by L9C16 CHO cells. Wild type MIS or mutant 103 were analyzed under reducing and non-reducing conditions, before and after digestion with plasmin.

Figure 10:
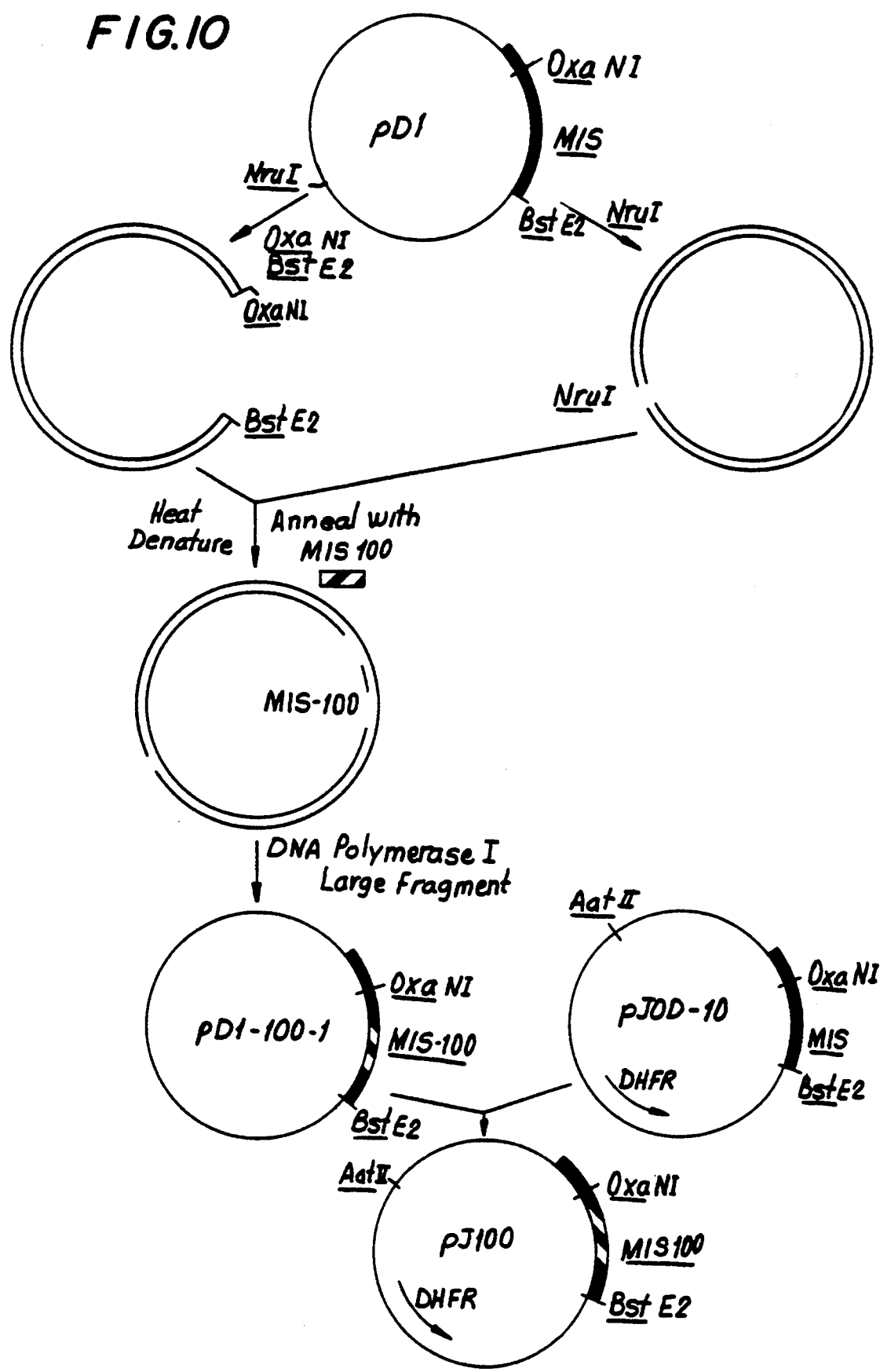

FIG. 10 is a schematic outline of the construction of plasmid pJ100.

Figure 11:
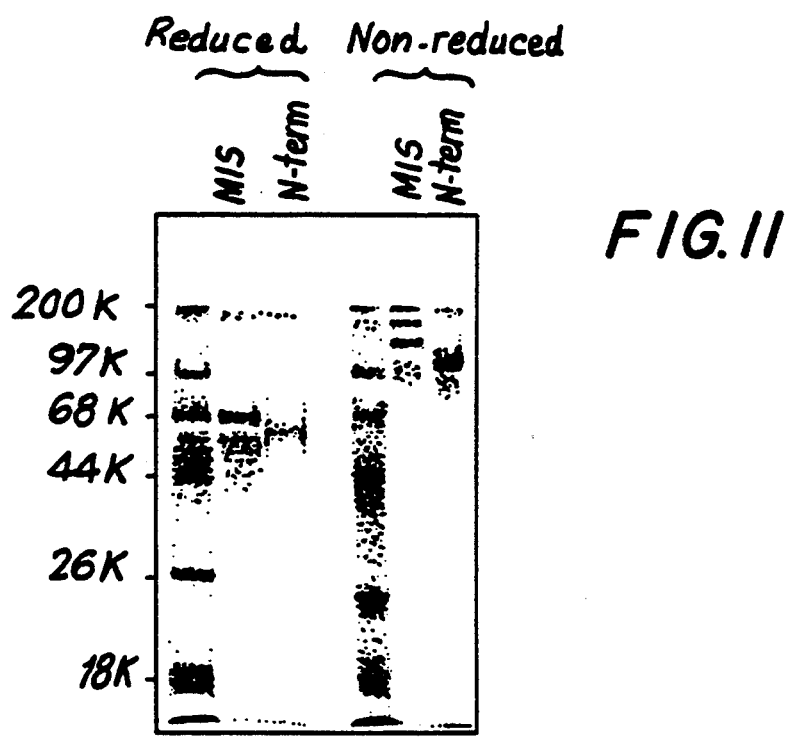

FIG. 11 is a SDS-PAGE analysis of purified N-terminal dimer produced by L7118 CHO cells.

Figure 12A:
Figure 12B:
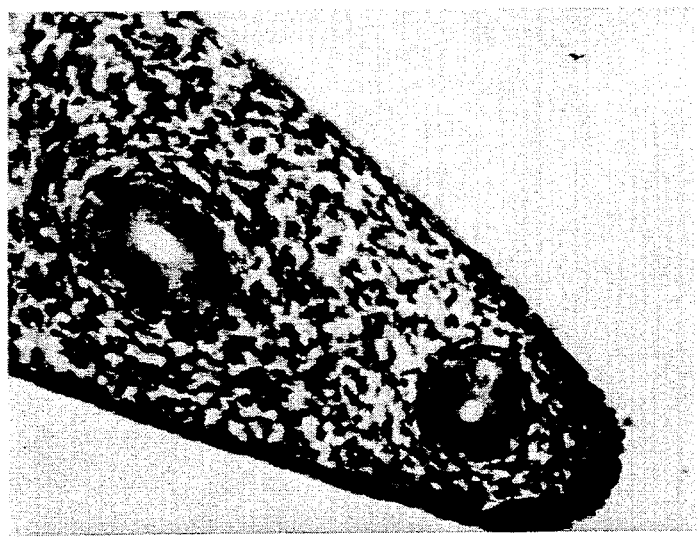
Figure 12C:

FIG. 12 depicts regression of the Mullerian duct by a combination of the N- and C-terminal dimers. Panel A shows regression in the presence of both the N- and C-terminal dimers. Panel B shows regression in the presence of the N-terminal dimer alone. Panel C shows regression in the presence of buffer.

DETAILED DESCRIPTION OF THE INVENTION

In order that the invention herein described may be more fully understood, the following detailed description is set forth.

In the description, the following terms are employed:

cDNA clone—A clone containing a DNA insert that was synthesized from mRNA and which does not contain introns. The vector can be a plasmid or a phage.

Genomic clone—A clone containing a DNA insert which is a fragment of a genome (i.e., isolated from total cellular DNA). It can contain introns which interrupt the protein coding region of the gene. The vector can be a plasmid, a phage or a cosmid.

Exon—Portions of the gene which after transcription are maintained in the mRNA following splicing of the precursor RNA.

Intron—Portions of the gene which are spliced out after transcription.

Recombinant DNA Molecule or Hybrid DNA—A molecule consisting of segments of DNA from different genomes which have been joined end-to-end outside of living cells and able to be maintained in living cells.

Expression Control Sequence—A sequence of nucleotides that controls and regulates expression of genes when operatively linked to those genes. They include the lac system, the β-lactamase system, the trp system, the tac and trc systems, the major operator and promoter regions of phage λ, the control region of fd coat protein, the early and late promoters of SV40, promotoers derived from polyoma virus and adenovirus, metallothionine promoters, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells and their viruses or combinations thereof. For mammalian cells the gene can be linked to a eukaryotic promoter such as that for the SV40 early region coupled to the gene encoding dihydrofolate reductase and selectively amplified in Chinese hamster ovary cells to produce a cell line containing many copies of actively transcribed eukaryotic genes.

MIS-Like Polypeptide—A polypeptide displaying a biological or immunological activity of an MIS protein. As used herein, the phrase "biological activity of an MIS protein" shall be understood to mean that the MIS-like polypeptide has a cross section of biological activity which is substantially similar to that of a natural MIS protein (e.g., it is able to stimulate regression of the Mullerian ducts and is cytotoxic to one or more types of ovarian tumor cells, for example, the cell line HOC-21, or inhibits growth of endometrial cancer, and preferably, it both stimulates regression of the Mullerian ducts and is cytotoxic to one or more types of endometrial or ovarian tumor cells). As used herein, the phrase "immunological activity of an MIS protein" shall be understood to mean the ability of an MIS-like polypeptide to cross-react with an antibody which is specific for a natural MIS protein. An example of such an antibody is disclosed in U.S. Pat. No. 4,487,833.

A MIS-like polypeptide may include amino acids in addition to those of a native MIS protein or it may not include all of the amino acids of native MIS protein. For example, it may include an N-terminal methionine. Also, this polypeptide may be a mature protein or an immature protein or a protein derived from an immature protein (for example, a protein wherein only a portion of the signal sequence has been cleaved). Examples of such polypeptides are derivatives of MIS polypeptides which have been prepared by modification of the MIS amino acid sequence to achieve an improvement in properties, e.g., greater storage stability or increased half-life in vivo. As used herein, the phrase "MIS-like polypeptides derived therefrom" shall be understood to mean not only a MIS-polypeptide (e.g., bovine MIS or human MIS) but also various related polypeptides of the types described in this paragraph.

Figure 1:
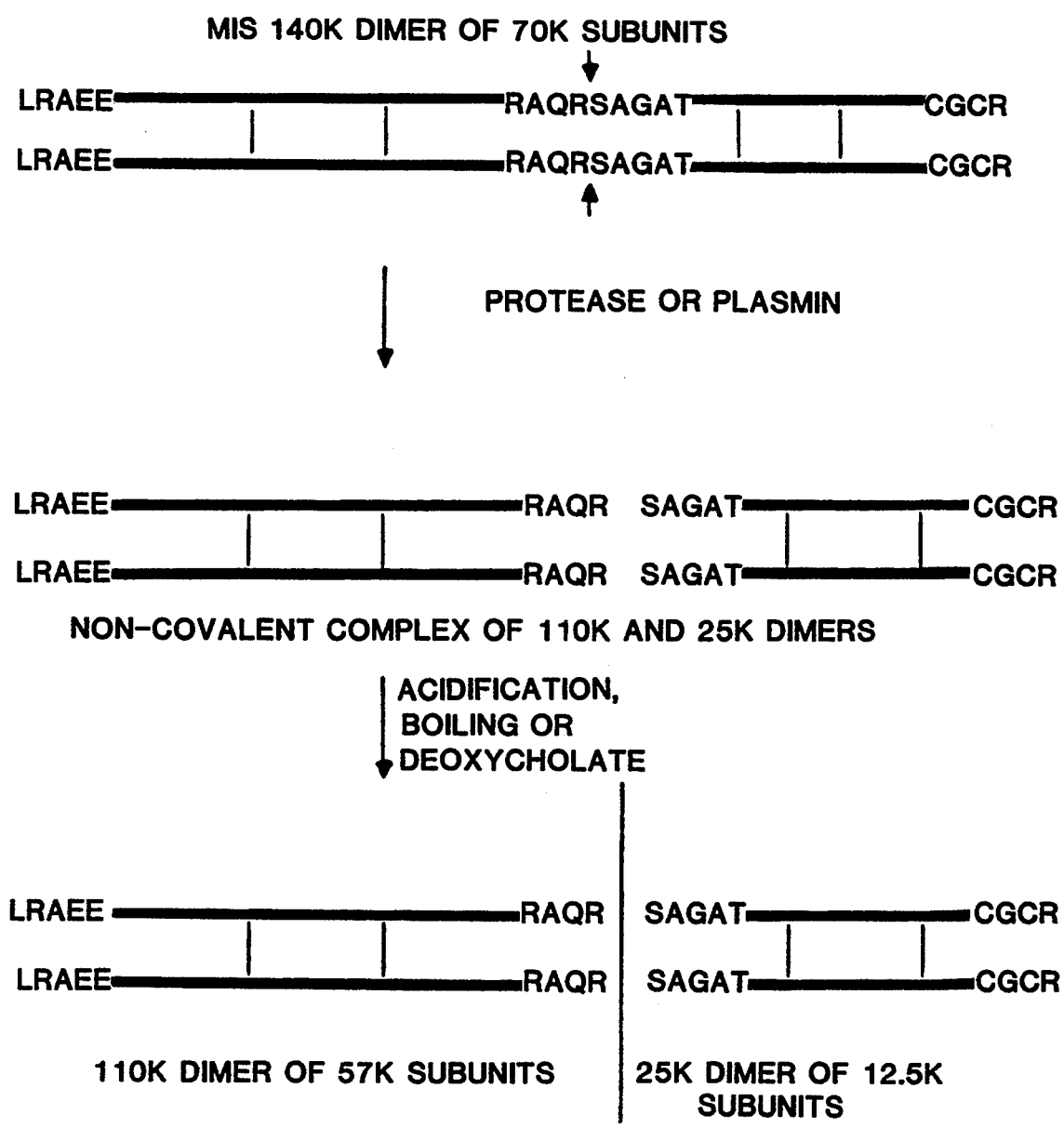
FIG. 1 is a schematic description of one process for producing N-terminal and C-terminal dimers of this invention from a dimer of a human MIS.
Figure 2A:
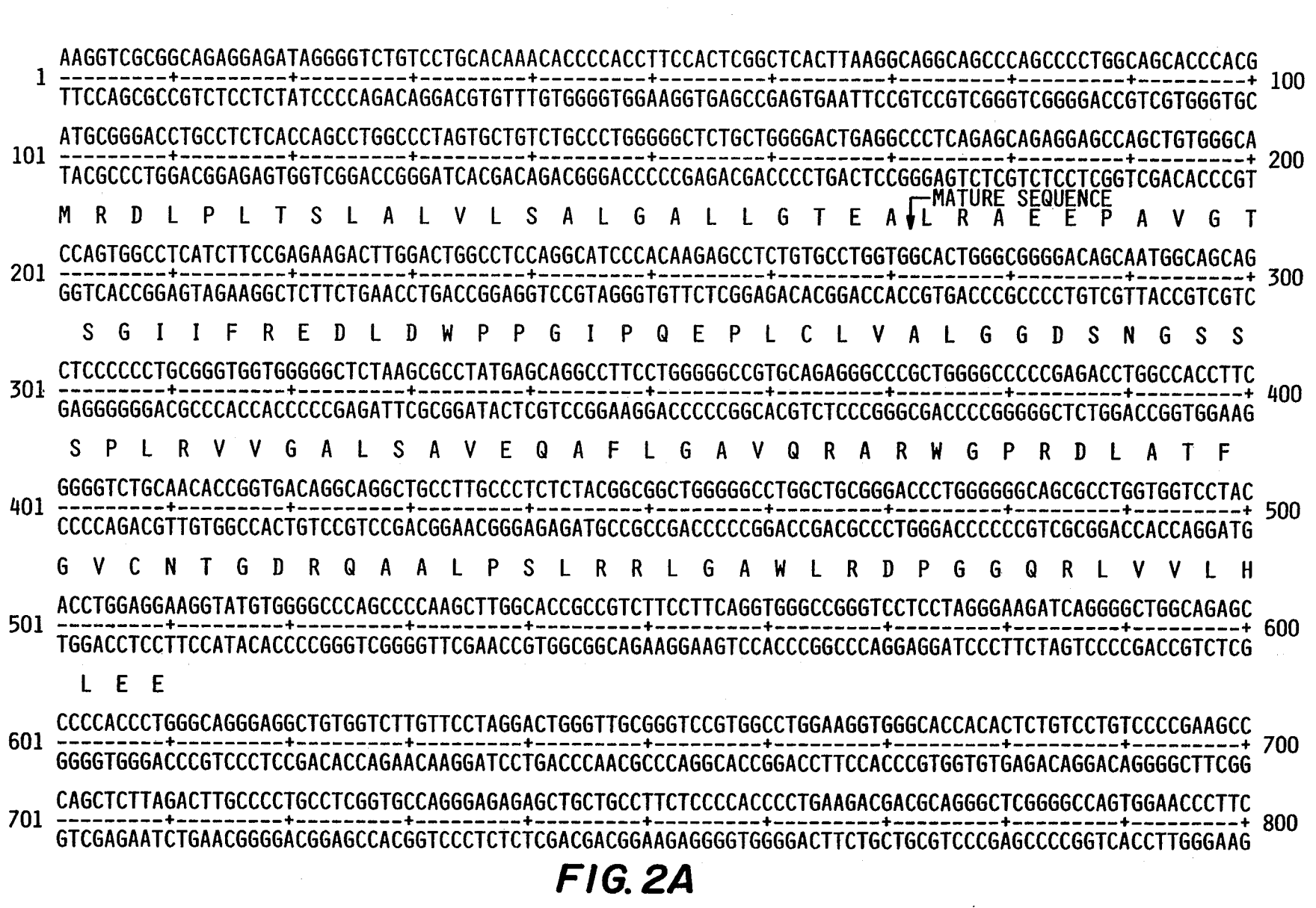
Figure 2B:
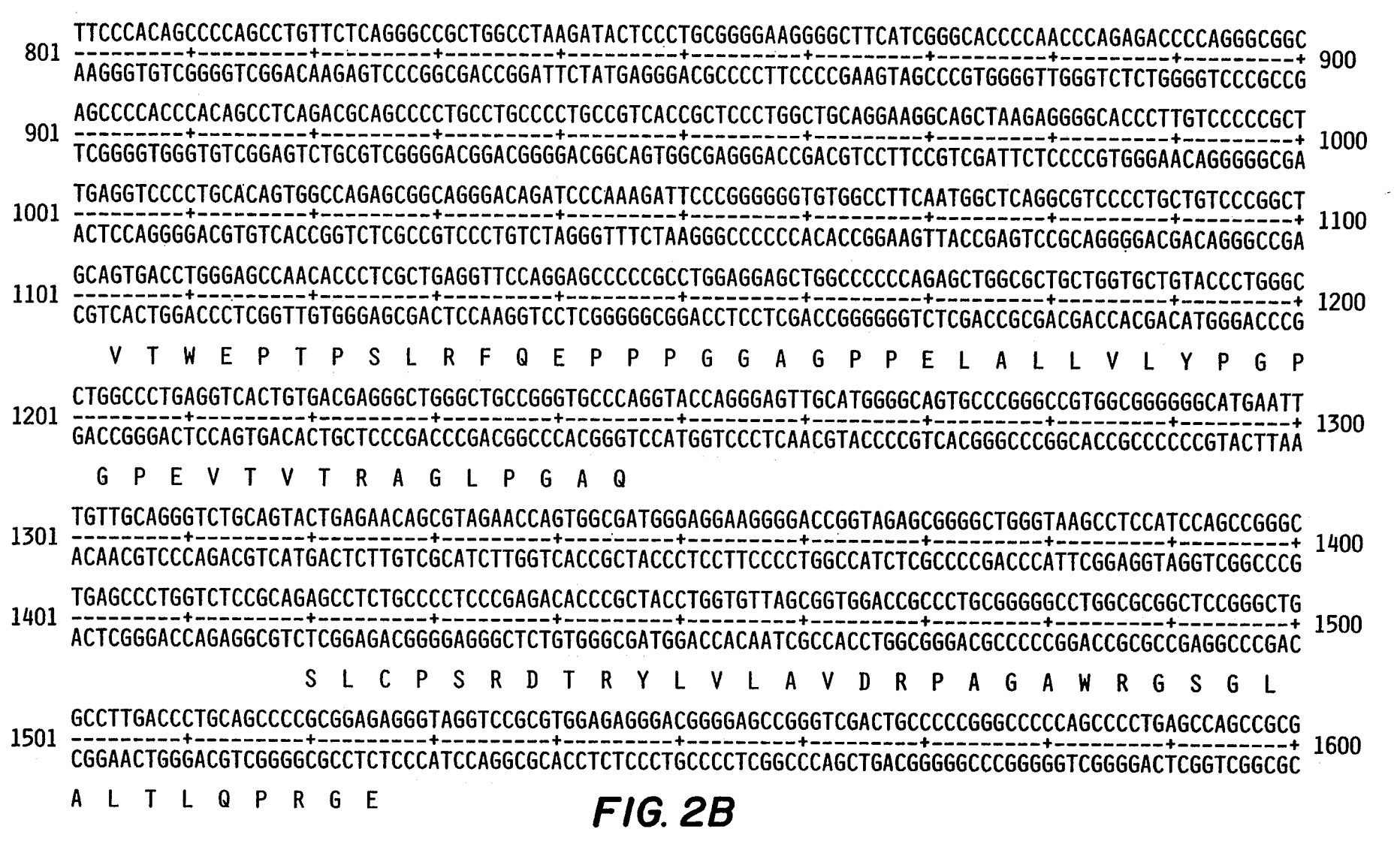
Figure 2C:
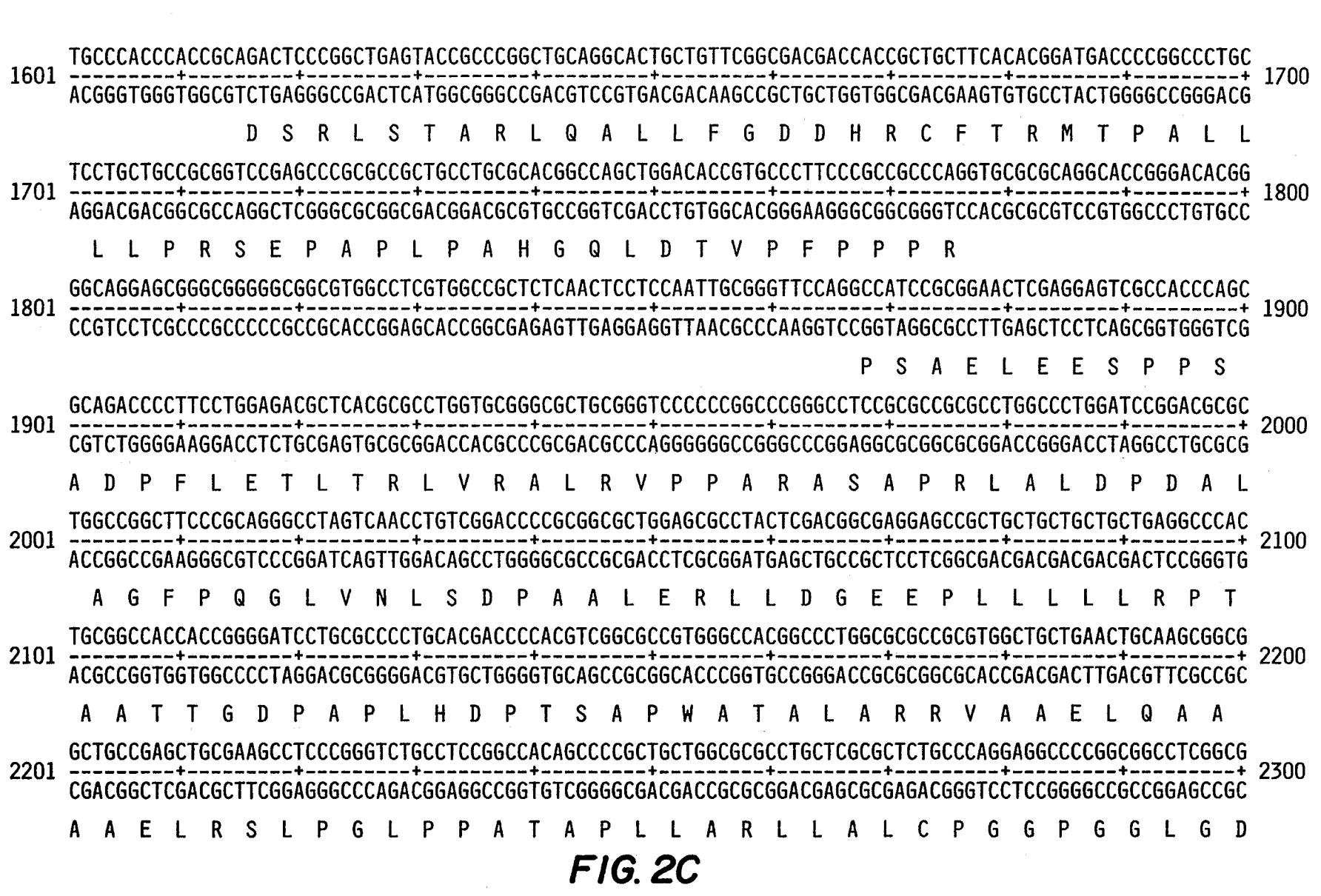
Figure 2D:
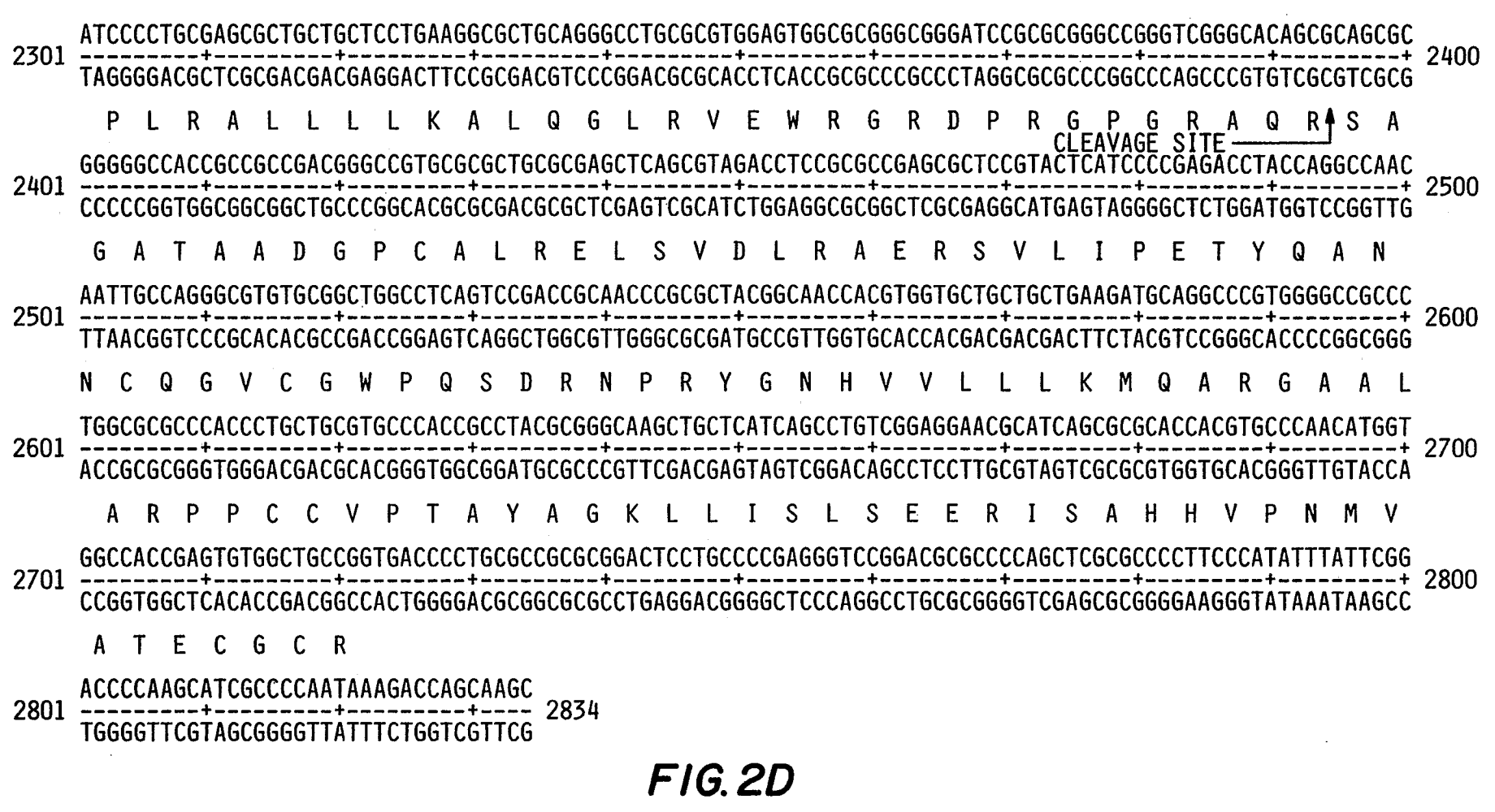

The N-terminal and C-terminal dimers of MIS-like polypeptides of this invention are characterized in that they are produced from a dimer of an MIS-like polypeptide by cleavage between Arg-Ser in the sequence corresponding to RAQRSAGAT of human or bovine MIS (see FIG. 1). For example, in the human MIS of FIG. 2, that Arg-Ser cleavage site occurs between $Arg_{427}$ and $Ser_{428}$ of mature human MIS. In bovine MIS of FIG. 3, the Arg-Ser cleavage site occurs between $Arg_{442}$ and $Ser_{443}$ of mature bovine MIS. In other MIS-like polypeptides, the Arg-Ser cleavage site may be easily located by aligning the sequences with those of mature bovine or human MIS for maximum homology using conventional techniques known in the art.

Thus, two examples of N-terminal dimers of this invention are those comprising disulfidelinked monomers having the following amino acid sequences:

(a) REEVFSTSALPREQATGSGALIFQQAWDWPLSSLWLP
GSPLDPLCLVTLHGSGNGSRAPLRVVGVLSSYEQAFLEAVRRTHWGL
SDLTTFAVCPAGNGQPVLPHLQRLQAWLGEPGGRWLVVLHLEEVTWE
PTPLLRFQEPPPGGASPPELALLVVYPGPGLEVTVTGAGLPGTQSLC
LTADSDFLALVVDHPEGAWRRPGLALTLRRRGNGALLSTAQLQALLF
GADSRCFTRKTPALLLLLPARSSAPMPAHGRLDLVPFPQPRASPEPE
EAPPSADPFLETLTRLVRALAGPPARASPPRLALDPGALAGFPQGQV
NLSDPAALERLLDGEEPLLLLLPPTAATTGVPATPQGPKSPLWAAGL
ARRVAAELQAVAAELRALPGLPPAAPPLLARLLALCPGNPDSPGGPL
RALLLLKALQGLRAEWRGRERSGSARAQR or portions there-
of displaying the biological activity of an
MIS-like polypeptide
(the monomer of an N-terminal dimer of a bovine MIS);

and (b) LRAEEPAVGTSGLIFREDLDWPPGIPQEPLCLVALGG
DSNGSSSPLRVVGALSAYEQAFLGAVQRARWGPRDLATFGVCNTGDR
QAALPSLRRLGAWLRDPGGQRLVVLHLEEVTWEPTPSLRFQEPPPGG
AGPPELALLVLYPGPGPEVTVTRAGLPGAQSLCPSRDTRYLVLAVDR
PAGAWRGSGLALTLQPRGEDSRLSTARLQALLFGDDHRCFTRMTPAL
LLLPRSEPAPLPAHGQLDTVPFPPPRPSAELEESPPSADPFLETLTR
LVRALRVPPARASAPRLALDPDALAGFPQGLVNLSDPAALERLLDGE
EPLLLLLRPTAATTGDPAPLHDPTSAPWATALARRVAAELQAAAAEL
RSLPGLPPATAPLLARLLALCPGGPGGLGDPLRALLLLKALQGLRVE
WRGRDPRGPGRAQR or portions thereof displaying
the biological activity of an MIS-like polypeptide (the monomer of an N-terminal dimer of a human MIS).

The C-terminal dimers of this invention are characterized by two disulfide-linked monomeric amino acid sequences of about 109 amino acids. They have a molecular weight of about 25K, each amino acid monomer chain having a molecular weight of about 12.5K. The N-terminal dimers of this invention are characterized by two disulfide-linked monomeric amino acid sequences of about 427 amino acids. They have a molecular weight of between about 110 and 115K, each monomeric amino acid chain having a molecular weight of about 57K. The two chains of both the C-terminal dimer and the two chains of the N-terminal dimer may be separated from each other under reducing conditions.

Two examples of C-terminal dimers of this invention are those comprising disulfide-linked monomers having the following amino acid sequences:

(a) SAGAAAADGPCALRELSVDLRAERSVLIPET
YQANNCQGACGWPQSDRNPRYGNHVVL
LLKMQARGATLARPPCCVPTAYTGKLLISL
SEERISAHHVPNMVATECGCR or portions
thereof displaying the biological
activity of an MIS-like polypeptide (the monomer of a C-terminal dimer of a bovine MIS); and (b) SAGATAADGPCALRELSVDLRAE
RSVLIPETYQANNCQGVCGWPOSDRNP
RYGNHVVLLLKMQARGAALARPPCCV
PTAYAGKLLISLSEERISAHHVPNMVATEC
GCR or portions thereof displaying
the biological activity of an MIS-like
polypeptide (the monomer of a C-terminal dimer of a human MIS).

The cleaved dimers of this invention may be produced in several ways. In one embodiment, an MIS-like polypeptide is isolated and purified from Sertoli cells using processes such as those described in published European patent application 221,761. These dimeric polypeptides having a molecular weight of about 140K, are then treated with plasmin, trypsin, or other proteases including serum proteases, to generate the N-terminal and C-terminal dimers of this invention. Typically, the N-terminal and C-terminal dimers produced by such plasmin or protease-induced Arg-Ser cleavage remain in non-covalent association with each other.

Although compositions of such associated dimers are useful in the various oncological and contraception applications of this invention, the N-terminal and C-terminal dimers may also be separated from each other by boiling, acidification or treatment with a detergent such as deoxycholate and used separately or together in the compositions and methods of this invention.

In a second embodiment of the processes of this invention for producing novel MIS dimers, the dimers are produced from MIS-like polypeptides produced in unicellular hosts transformed with an expression vector carrying a DNA sequence coding for such MIS-like polypeptides. Such transformed hosts are, for example, described in published European patent application 221,761, which application is incorporated by reference herein. Specific examples of such expression vectors were also deposited in a recognized culture collection and described in that application. These include, for example, *E. coli* JMB3 (p.BG311.bmis) [IVI 10090] and *E. coli* JA221 (p.BG312.hmis) [IVI 10089]. These hosts carry animal cell expression vectors that are useful in transforming animal cells to produce bovine (bmis) and human (hmis), respectively.

In this embodiment of the present invention, the transformed host is cultured to produce the MIS-like polypeptide. That polypeptide is then correctly folded to form its disulfide bridges and treated as above with plasmin, trypsin, or other protease, to produce the desired dimers. Again, the N-terminal and C-terminal dimers typically remain in non-covalent association after such treatment. However, if desired, they may be separated by boiling, acid treatment or treatment with a detergent such as deoxycholate before they are used in the compositions and methods of this invention.

In a third embodiment of the processes of this invention for production of novel MIS dimers, the dimers may be produced using recombinant DNA technology. For example, a DNA sequence coding for the amino acid sequence of the monomer of either the C-terminal or N-terminal dimers of MIS-like polypeptides, or both, may be employed using appropriate expression vectors and expression control sequences to transfect conventional unicellular hosts. Those transformed hosts then produce the monomer that characterizes the desired MIS dimer on fermentation. The required disulfide bridges may then be formed either before, during or after isolation of the produced monomer to produce the desired dimer.

Various techniques well known in the art may be used to isolate a DNA sequence coding for the desired monomer. For example, the processes described in published European patent application 221,761 may be employed to isolate a DNA sequence coding for a mature or immature MIS-like polypeptide. The nucleotide and amino acids of two such polypeptides are depicted in FIGS. 2 and 3 of this application. They are also carried by plasmids pBG311.bmis and pBG312.hmis deposited in connection with the published European patent application 221,761 and whose construction is described therein.

The DNA sequences coding for the monomers that characterize the desired dimer may then be isolated from the larger DNA sequences by any conventional technique known to those of skill in the art. For example, the larger DNA sequence may be cut with a restriction enzyme at a site, originally present or constructed by site directed mutagenesis, at or near to the "Arg-Ser" cleavage between the N-terminal and C-terminal monomers. If the restriction cut is between the codons that code for the Arg-Ser cleavage site between the N-terminal and C-terminal dimers of MIS, the produced DNA is ready for insertion into an expression vector and transformation into a unicellular host for production of the desired monomer. If the restriction site is upstream or downstream of the Arg-Ser cleavage site, the resulting DNA sequence will need to be shortened by digestion, e.g., using Bal 31, or lengthened by a synthetic oligomer to produce the desired DNA sequence.

A wide variety of host/expression vehicle combinations may be employed in expressing these DNA sequences. For example, useful expression vehicles may consist of segments of chromosomal, non-chromosomal and synthetic DNA sequences, such as various known derivatives of SV40 and known bacterial plasmids, e.g., plasmids from *E. coli* including col E1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single-stranded DNA phages and vectors derived from combinations of plasmids and phage DNAs such as plasmids which have been modified to employ phage DNA or other expression control sequences or yeast plasmids such as the 2 μ plasmid or derivatives thereof. For animal cell expression, the preferred expression vectors are pBG311 and pBG312 in Chinese hamster ovary (CHO) cells.

Within each specific expression vehicle, various sites may be selected for insertion of the DNA sequences. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that an expression vehicle useful in this invention need not have a restriction endonuclease site for insertion of the chosen DNA fragment. Instead, the vehicle could be joined to the fragment by alternative means.

Various expression control sequences may also be chosen to effect the expression of the DNA sequences. These expression control sequences include, for example, the lac system, the β-lactamase system, the trp system, the tac system, the trc system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, promoters for mammalian cells such as the SV40 early promoter, adenovirus late promoter and metallothionine promoter, and other sequences known to control the expression of genes of prokaryotic or eukaryotic cells or their viruses and various combinations thereof. In mammalian cells, it is additionally possible to amplify the expression units by linking the gene to that for dihydrofolate reductase and applying a selection to host Chinese hamster ovary cells.

For expression, DNA sequences are operatively-linked to one or more of the above-described expression control sequences in the expression vector. Such operative linking, which may be effected before or after the chosen DNA sequence is inserted into an expression vehicle, enables the expression control sequences to control and promote the expression of the DNA sequence.

The vector or expression vehicle, and in particular the sites chosen therein for insertion of the selected DNA fragment and the expression control sequence employed in this invention, is determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a particular DNA sequence is determined by a balance of these factors, not all selections being equally effective for a given case.

It should also be understood that the DNA sequences coding for the monomers of the dimers of this invention that are inserted at the selected site of an expression vehicle may include nucleotides which are not part of the actual DNA sequence coding for desired monomer. For example, the DNA sequences may be fused in the same reading frame in an expression vector to at least a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired DNA sequence or improve purification or permit secretion, of the monomer from the host cell. The DNA sequence may alternatively include an ATG start codon, alone or together with other codons, fused directly to the sequence encoding the first amino acid of the desired monomer. Such constructions enable the production of, for example, a methionyl or other peptidyl MIS monomers. This N-terminal methionine or peptide may either then be cleaved intra- or extra-cellularly by a variety of known processes or the monomers with the methionine or peptide attached may be used, uncleaved, in preparing the dimers of this invention.

The expression vector containing the DNA sequence coding for a MIS monomer is employed in accordance with this invention to transform an appropriate host so as to permit that host to express the monomer for which the DNA sequence codes. Such useful expression hosts may include strains of E. coli, such as E. coli C600, E. coli ED8767, E. coli DH1, E. coli LE392, E. coli HB 101, E. coli X1776, E. coli X2282, E. coli MRCI, E. coli BNN102, E. col JM83, E. coli JA221, and strains of Pseudomonas, Bacillus, and Streptomyces, yeasts and other fungi, animal hosts, such as CHO cells, COS cells or mouse cells, other animal (including human) hosts, plant cells in culture or other hosts.

The selection of an appropriate host is controlled by a number of factors recognized by the art. These include, for example, compatibility with the chosen vector, toxicity of proteins encoded by the hybrid plasmid, susceptibility of the desired protein to proteolytic degradation by host cell enzymes, contamination or binding of the protein to be expressed by host cell proteins difficult to remove during purification, ease of recovery of the desired protein, expression characteristics, biosafety and cost. A balance of these factors must be struck with the understanding that not all host vector combinations may be equally effective for either the cloning or expression of a particular recombinant DNA molecule.

It should be understood that the monomers (prepared in accordance with this invention in those hosts) may include polypeptides in the form of fused proteins (e.g., linked to prokaryotic, eukaryotic or combination N-terminal segment to direct excretion, improve stability, improve purification or improve possible cleavage of the N-terminal segment), in the form of a precursor of the monomer (e.g., starting with all or parts of a MIS-like polypeptide signal sequence or other eukaryotic or prokaryotic signal sequences), in the form of the mature monomer, or in the form of an f-met-monomer.

One particularly useful form of a polypeptide in accordance with this invention, or at least a precursor thereof, is a MIS monomer with an easily cleaved amino acid or series of amino acids attached to the amino terminus. Such construction allows synthesis of the polypeptide in an appropriate host, where a start signal that may not be present in the monomer is needed, and then cleavage in vivo or in vitro of the extra amino acids to produce the desired monomer. Such methods exist in the art. See, e.g., U.S. Pats. Nos. 4,332,892, 4,338,397, and 4,425,437. The monomers may also be glycosylated, like native MIS protein, unglycosylated, or have a glycosylation pattern different than that of native MIS protein. Such glycosylation will result from the choice of host cell or post-expression treatment chosen for the particular monomer.

The monomers of the invention also include polypeptides that are coded for on expression by DNA sequences characterized by different codons for some or all of the codons of the native MIS for which the monomer codes. These substituted codons may code for amino acids identical to those coded for by the codons replaced but result in higher yield of the polypeptide. Alternatively, one or a combination of codons may be replaced, leading to amino acid replacement or to a longer or shorter monomer. Such replacements or modifications may alter the properties of the monomer in a useful way (e.g., increase the stability, increase the solubility or increase the therapeutic activity).

The MIS dimers of this invention are useful alone or in combination as anti-cancer drugs. For example, such compositions may comprise an anti-cancer effective amount of an MIS dimer of this invention and a pharmaceutically acceptable carrier. Such therapies generally comprise a method of treating patients in a pharmaceutically acceptable manner with those compositions.

Generally, the pharmaceutical compositions of the present invention may be formulated and administered using methods similar to those used for other pharmaceutically important polypeptides (e.g., alpha-interferon). Thus, the polypeptides may be stored in lyophilized form, reconstituted with sterile water just prior to administration, and administered intravenously. Preferably, the pharmaceutical formulation of the present invention will be administered in dosages and modes of administration similar to those that have been used for MIS protein as disclosed in U.S. Pat. No. 4,510,131, the disclosure of which is hereby incorporated by reference.

According to this invention, MIS dimers may be administered to the patient in any pharmaceutically acceptable dosage form, including those which may be administered to a patient intravenously as bolus or by continuous infusion over a period of minutes, hours, days, weeks or months, intramuscularly, subcutaneously, intracutaneously, intra-articularly, intrasynovially, intrathecally, periostally, or by oral, topical, or inhalation routes. MIS dimers may also be administered intratumorally, peritumorally, intralesionally or periolesionally to exert local as well as systemic therapeutic effects.

The most effective mode of administration and dosage regimen of MIS dimers will depend upon the type of disease to be treated, the severity and course of that disease, previous therapy, the patient's health status and response to the MIS dimers and the judgment of the treating physician. MIS dimers may be administered to the patient at one time or over a series of treatments until the desired suppression of cancer of the female genital tract is achieved.

The MIS dimers of this invention are also useful alone or in combination in compositions and methods for contraception. For example, such compositions may comprise an effective amount of the MIS dimers of this invention and a pharmaceutically acceptable carrier. An effective amount of the MIS dimers of this invention is one which is sufficient to achieve contraception in an ovulating human or animal.

The most effective mode of administration and dosage regimen of MIS dimers will depend upon the age, weight, physical condition, medical history, sensitivity of the patient and the judgment of the treating physician. The MIS dimers of this invention may be administered to the patient in any pharmaceutically acceptable dosage form, including administration as a bolus over a period of time in discreet and separable dosages.

In order that this invention may be better understood, the following examples are set forth. These examples are for purposes of illustration only and are not to be construed as limiting the scope of the invention in any manner.

EXAMPLES

Purification Of MIS

We produced human recombinant MIS from CHO cell line 311-2A9B7 (described in published European patent application 221,761) and from CHO cell line L258B9 transfected with the human MIS gene. All of the following examples used human recombinant MIS from CHO cell line L258B9.

We produced cell line L258B9 as described below. 18.9 μg of plasmid pBG311.hmis was linearized with Asp700 and 1.1 μg of pAdD26 was linearized with StuI and introduced into CHO DHFR− cells using the calcium phosphate protocol as described in S. J. Scahill et al., "Expression and Characterization of the Product of a Human Immune Interferon cDNA Gene In Chinese Hamster Ovary Cells, " *P.N.A.S.*, 80, 4654–4658 (1983). The construction of pAdD26 is described in R. J. Kaufman and P. A. Sharp, "Construction of a Modular Dihydrofolate Reductase cDNA Gene: Analysis of Signals Utilized for Efficient Expression," *Mol. Cell. Biol.*, 2, 1304–1319 (1982). Transformants were selected as described below. We selected CHO cell lines expressing the full length form of MIS in a α-minimum essential medium without ribonucleosides and deoxyribonucleosides (α-medium), which was supplemented with 10% dialyzed fetal bovine serum (FBS). A cell line L258 was obtained expressing about 0.5 mg of MIS per liter of culture medium per day. This cell line was plated in 30 nM methotrexate in order to increase the MIS copy number and thereby increase expression. The cell line thus obtained, L258B9, was produced about 3 mg of MIS per liter per day.

We grew the transfected cells at 37° C. in a minimum essential medium without ribonucleosides and deoxyribonucleosides, which was supplemented with 10% fetal calf serum. The conditioned medium was clarified by filtration and concentrated 15-fold by ultrafiltration. We purified the MIS from the concentrate by affinity chromatography on a M10.6 immunoaffinity column using Mab 10-6, a monoclonal antibody raised against the recombinant protein. We then eluted MIS from the affinity matrix with 2M NaSCN, 150 mM NaCl, 15 mM sodium phosphate, pH 6.3, essentially as described in J.-Y. Picard and N. Josso, *Mol. Cell. Endocrinol.*, 84, pp. 23–29 (1984). The chaotrope was removed and replaced with MIS storage buffer (10% glucose, 300 mM NaCl, 10 mM HEPES, pH 7.5) in a P-6DG desalting column (Bio-Rad). We aliquoted and stored the final preparation at −70° C.

We also metabolically labeled the MIS with [$^{35}$S] cysteine by pulse - labelling the transfected CHO cells (L258B9) for 80 minutes with [$^{35}$S] cysteine (approximately 600 Ci/mmol) in cysteine-free minimum essential medium containing 500 μCi/ml of the radioactive amino acid and then chasing the label for 20 hours with complete growth medium. The recombinant MIS was purified from the labelling medium by immune precipitation using the M10.6 monoclonal antibody and eluted from the immune complex with nonreducing electrophoresis sample buffer. After releasing the MIS with nonreducing buffer, a portion of the sample was reduced with 2% 2-mercaptoethanol.

On SDS-polyacrylamide gels, the affinity purified protein migrated under reducing conditions with an apparent mass of 70K. Under non-reducing conditions, the protein migrated with an apparent mass of 140K. In addition to these dimeric species of MIS, we observed other higher molecular weight disulfide-linked oligomers. These larger forms also were obtained with radioactive MIS that was pulselabeled with [$^{35}$S] cysteine and analyzed directly by SDS-PAGE and with preparations that were disrupted with SDS in the presence of 50 mM iodoacetic acid, indicating that the oligomers were not generated by sample preparation. While the organization of disulfide bonds in MIS has not been determined, the presence of the oligomers suggests that one or more cysteines have free sulfhydryl groups. The aminoterminal sequence of the purified protein was Leu-Arg-Ala-Glu-Glu-Pro-Ala-Val-Gly-Thr, which is consistent with the amino terminus of mature MIS.

In addition to 70K MIS, a fraction of the purified protein exists as a 57K form. The amount of that form ranges between about 5 and 20% of the total protein. A small fraction with an apparent mass of 12K was also observed, suggesting that the 57K and 12K products may be generated by proteolysis. Under nonreducing conditions, the 12K species migrated as a 25K dimer. We then subjected the 57 and 12K dimers to protein sequencing.

The sequence of the N-terminal dimer was Leu-Arg-Ala-Glu-Glu-Pro-Ala-Val-Gly-Thr, indicating that it was derived from the amino terminus of MIS, while the sequence of the C-terminal fragment was Ser-Ala-Gly-Ala-Thr-Ala-Ala-Asp-Gly-Pro, indicating that it was derived from near the carboxyl terminus. Thus, 5–20% of the protein in MIS preparations is cleaved at a site 109 amino acids from the carboxyl terminus (FIG. 1).

Plasmin Digestion Of Purified MIS

We diluted the purified MIS 1:1 with water and incubated it at room temperature with plasmin (Sigma) at a constant MIS to plasmin ratio of 25:1 (w/w). We incubated MIS samples with the plasmin at room temperature in 5% glucose, 150 mM NaCl, 5 mM HEPES, pH 7.4, for between about 10 to 120 minutes, typically 60 minutes. The proteolysis was stopped by diluting the samples with electrophoresis sample buffer and heating the preparations at 65° C. for 10 minutes. We analyzed the cleavage products by SDS-PAGE on 12% polyacrylamide gels using the Laemmli system [U. K. Laemmli, Nature, 227, pp. 680-85(1970)] and staining with Coomassie Brillant Blue. The reactions for organ culture assays were quenched by adding fetal bovine serum to 10% and for gel filtration by adding acetic acid to 1M. The organ culture assay was carried out as described in P.K. Donahoe et al., J. Surg. Res., 23, pp. 144-48 (1977).

We observed that when purified MIS was incubated with plasmin for 1 hour, the protein was cleaved into a 57K species and a 12K species. The sizes of the species and subsequent sequencing of the cleavage products revealed that they were the same species which we had previously observed as minor components in the purified MIS preparations. In the absence of a reducing agent, the 12K species migrated as a 25K dimer and the 57K species migrated as a 110K dimer.

Within the 2 hour incubation period, only the 57K and 12K species were generated. With longer incubation times or with higher plasmin concentrations, an additional cleavage within the 57K species was observed, generating a 33K and a 24K fragment. MIS could also be selectively cleaved with trypsin to generate the 57 and 12K species, with the reaction being less controlled. With trypsin, both species were susceptible to further digestion.

We then subjected the 57 and 12K dimers produced by plasmin digestion to protein sequencing. Samples containing either 0.5 nmol of intact protein or 0.25 nmol of the plasmin-derived fragments were subjected to automated Edman degradation in an Applied Biosystems (ABI) 470 A gas phase Sequencer in the presence of Polybrene [R. M. Hewich et al., J. Biol Chem., 256, pp. 7990-97(1981)]. PTH amino acids were analyzed on-line using an ABI 120 PTH analyzer. The amino acid composition of parallel aliquots were determined in a Beckman System 6300 amino acid analyzer. The sequence of the N-terminal dimer was Leu-Arg-Ala-Glu-Glu-Pro-Ala-Val-Gly-Thr, indicating that it was derived from the amino terminus of MIS, while the sequence of the C-terminal fragment was Ser-Ala-Gly-Ala-Thr-Ala-Ala-Asp-Gly-Pro, indicating that it was derived from near the carboxyl terminus.

As previously described, the 57 and 12K fragments from a preparation of affinity-purified MIS were isolated by preparative SDS-PAGE and subjected to amino-terminal sequencing. The observed sequences were identical to those generated from plasmin-treated MIS. Although the source of the protease in conditioned medium responsible for the processing is not known, the sequencing results indicate that it and plasmin cleave MIS at the same site.

Purification and Properties of the Carboxyl-Terminal Dimer of MIS

While digestion by plasmin caused the quantitative cleavage of the MIS, the resulting dimers remained associated as a noncovalent complex The dimers could be separated by acidifying the sample with 1M acetic acid, by boiling, or by detergent treatment with deoxycholate. Also, a nonionic or another ionic detergent which dissociates the fragments without a concomitant loss of their biological activity may be used. Specifically, 2 mg plasmin-treated MIS in 1M acetic acid was subjected to gel filtration on a P-150 column (1.5×40 cm) in 1M acetic acid at a flow rate of 2 ml/h. Fifty 0.5 ml fractions were collected. Samples were tested for absorbance at 280 nm and for composition by SDS-PAGE for gel analysis, aliquots were dried with a Speed Vac Concentrator (Savant) and resuspended in electrophoresis sample buffer.

In 1M acetic acid, both MIS dimers were soluble and could be separated by gel filtration chromatography in acetic acid. The two dimers were completely resolved. After removal of the acetic acid by lyophilization, we found that the dimers were soluble in 4 mM HCl, as well as in PBS at neutral pH.

After boiling plasmin-cleaved MIS for 10 minutes, the C-terminal dimer remained soluble, while most of the N-terminal dimer precipitated and could be removed by centrifugation.

Alternatively, the two dimers were dissociated with 1% sodium deoxycholate as detailed below. Concentrations of sodium deoxycholate between 0.5% and 1.5% also dissociated the two dimers.

We then subjected the carboxyl-terminal dimer to amino acid analysis. Table I below shows theoretical and observed amino acid compositions for the dimer and for intact MIS.

TABLE I

| Amino acid | MIS Theoretical | MIS Actual | Dimer Theoretical | Dimer Actual |
|---|---|---|---|---|
| Cysteine | | | | |
| Aspartic acid | 32 | 32.6 | 8 | 8.1 |
| Threonine | 25 | 26.7 | 4 | 5.3 |
| Serine | 28 | 23.9 | 7 | 6.2 |
| Glutamic acid | 47 | 47.3 | 10 | 10.8 |
| Proline | 65 | 63.5 | 8 | 9.0 |
| Glycine | 49 | 49.0 | 8 | 8.5 |

TABLE I-continued

| Amino acid | MIS Theoretical | MIS Actual | Dimer Theoretical | Dimer Actual |
|---|---|---|---|---|
| Alanine | 71 | 70.8 | 15 | 14.6 |
| Valine | 28 | 26.9 | 8 | 6.2 |
| Methionine | | | | |
| Isoleucine | 5 | 5.6 | 3 | 2.6 |
| Leucine | 87 | 88.8 | 11 | 12.1 |
| Tyrosine | 6 | 7.0 | 3 | 2.6 |
| Phenylalanine | 9 | 9.1 | 0 | 0.7 |
| Histidine | 7 | 7.0 | 3 | 2.4 |
| Lysine | 3 | 4.0 | 2 | 2.0 |
| Arginine | 51 | 49.4 | 9 | 8.6 |

As shown in Table I, the theoretical and observed compositions of the dimer show a good correlation. In particular, the presence of 9 arginines (since arginine is the last amino acid in the fragment) supports that no other processing has occurred. For comparison, the theoretical and observed compositions for intact MIS are shown, which also demonstrate a good correlation.

We have shown below the activities of the various species in the organ culture assay (regression of the Mullerian duct). Both full length and plasmin - digested MIS caused regression of the Mullerian duct in the organ culture assay. The specific activity of the MIS was unaffected by the cleavage. The results are displayed in Table II.

TABLE II

| MIS Preparation** | 1:20 Dilution | Dose Response* 1:40 Dilution | 1:50 Dilution |
|---|---|---|---|
| intact MIS | 5 | 5 | |
| Plasmin-digested MIS | 5 | 5 | 3 |
| MIS + 1M acetic acid | 0 | 0 | |
| digested MIS + 1M acetic acid | 2–3 | 0 | |
| MIS + boiling | 3 | 0–1 | |
| Digested MIS + boiling | 0 | 0 | |
| C-terminal dimer isolated after acid treatment or boiling | 0 | 0 | |
| Digested MIS + deoxycholate | | | 3–4 |

*The dose response in measured by grades: 5 = 1:20 dilution; 4–5 = 1:40 dilution; 3 = 1:80 dilution; 2 = 1:160 dilution.
**All MIS concentrations were 330μg/ml, except that the C-terminal dimer isolated after acid treatment or boiling was used at 100μg/ml.

* The dose response is measured by grades: 5=1:20 dilution; 4-5=1:40 dilution; 3=1:80 dilution; 2=1:160 dilution. ** All MIS concentrations were 330 μg/ml, except that the C-terminal dimer isolated after acid treatment or boiling was used at 100 μg/ml.

These assays demonstrate that the plasmin-cleaved dimers when associated have similar activity in the assay to intact MIS. Plasmin digestion of the 140K dimer of MIS did not alter its activity in the organ culture assay. However, treatment with acid or boiling, although permitting dissociation of the two dimers, appears also to reduce the activity of both the intact MIS and cleaved MIS. Treatment with sodium deoxycholate permitted dissociation of the two fragments, and did not alter the activity of the intact and cleaved MIS.

Deoxycholate Dissociates The Non-Covalent Complex and Does Not Affect Biological Activity We digested 250 μg of human recombinant MIS (as prepared above in the Example entitled Purification of MIS) with 25 μg of plasmin in a 1 ml reaction containing 5 mM HEPES (pH 7.4), 150 mM NaCl, and 5% glucose for 60 min at 25° C. The reaction was stopped by adding soybean trypsin inhibitor to 100 ug/ml and the extent of digestion was analyzed by SDS-PAGE. This showed that the 140K dimer of MIS had been completely cleaved to generate a 110K N-terminal dimer and a 25K C-terminal dimer. It was previously reported that the N-terminal cleavage product was a trimer. This was apparently due to a gel artifact, which can be eliminated by using a modified Laemmli gel system as described below. FIG. 4 shows the results of a titration with plasmin as analyzed by SDS-PAGE under reducing and nonreducing conditions (1 μg per lane) on 10% gels using the Laemmli system (Laemmli, U. K., Nature, 237, 680-685 (1970)) with the following modifications. The concentration of Tris-HCl (pH 6.8) in the stacking gel was 125 mM and the concentration of Tris-HCl (pH 8.8) in the gel was 370 mM. Proteins were stained with Coomassie Brilliant Blue. The ratio of MIS to plasmin (weight/weight) was 10 (lane 2), 20 (lane 3), 40 (lane 4), or 80 (lane 5). Lane 1 contains undigested MIS. Under non-reducing conditions and with this gel system, the N-terminus migrates as a dimer.

We bound the non-covalent complex to an immunoaffinity matrix that was prepared according to the following procedure. A mouse monoclonal antibody M10.6 which was raised against human recombinant (obtained from CHO cell line 311-2A9B7) MIS and recognizes an epitope on the N-terminal domain, was purified from mouse ascites by a combination of protein A Sepharose and ion-exchange (Fast Q) chromatography, and coupled to Affigel-10 using the manufacturer's directions. We transferred 250 μl of this matrix containing the M10.6 antibody to a 1.5 ml Eppendorf tube and washed 3 times with PBS, 2 times with 2M NaSCN, and three times with PBS (1 ml per wash). We then added the plasmin cleaved MIS (1 ml) to the washed matrix, and rocked the Eppendorf tube for 90 min at 4° C. The matrix was then washed three times with PBS (1 ml per tube), and transferred to a disposable 2 ml glass pipet that had been plugged with siliconized glass wool.

The C-terminal dimer was eluted from the column with 1% sodium deoxycholate (10 mM HEPES, pH 8.0, 150 mM NaCl) which was applied in 6 fractions of 125 μl. SDS-PAGE showed that only the C-terminal dimer was eluted with this treatment (FIG. 5, lane 1). 10 μl of one of the deoxycholate fractions was analyzed in lane 1. We then washed the column with PBS (5 ml) and eluted with 2M NaSCN applied in 6 fractions of 125 μl. Ten μl of one of the 2M NaSCN fractions was analyzed in lane 2. These fractions contained both the N-terminal dimer and the C-terminal dimer. The gel conditions were similar to those described for FIG. 4, with the following exceptions. The acrylamide percentage of the stacking gel and gel was 7.5% and 12%, respectively. The concentration of Tris-HCl (pH 6.8) in the stacking gel was 62 mM and concentration of Tris-HCl (pH 8.8) in the gel was 400 mM. The concentration of Tris base and glycine in the running buffer were 50 mM and 500 mM, respectively.

To demonstrate that 1% sodium deoxycholate did not affect biological activity, we cleaved MIS with plasmin as described above, except that the MIS concentration was 667 μg/ml. 10 μl of this plasmin cleaved MIS was added to either an Eppendorf tube with 15 μl of MIS buffer (10 mM HEPES, pH 7.4, 300 mM NaCl, 10% glucose) or to a tube with 12.5 μl of MIS buffer and 2.5 μl of 10% sodium deoxycholate. The two tubes were incubated on ice for 5 min. We then added 88 μl of cold MIS buffer to both tubes. The tubes were maintained on ice for 3 hours, after which 1 ml of organ culture medium was added. The diluted samples were sterile filtered, and introduced in duplicate into the organ culture assay (Donahoe et al. *J. Surg. Res.*, 23, 141-148 (1977)) to measure biological activity. The sample not treated with deoxycholate produced grade 3 regression of the Mullerian duct in both assays, while the sample treated with deoxycholate produced grade 3 and grade 3-4 regression in the two assays. Thus, treatment of plasmin-cleaved MIS with deoxycholate did not affect biological activity.

Construction Of pD1

We constructed pD1 via a four way ligation shown in FIG. 6 with the following four fragements: 1) 271 bp StuI-MstII fragment form pGAP1.6; 2) 323 bp MstII - XhoI fragment from pMIS D/F; 3) 1299 bp XhoI - StuI fragment from pBG312.hmis; and 4) the 6251 bp StuI fragment from pBG312.hmis.

We inserted the 4.5 kb AflII fragment from chmis33 into the animal cell expression vectors pBG311 and pBG312 described by Cate et al. (Cell, 45, 685-698 (1986)), to produce pBG311.hmis and pBG312.hmis, respectively. pBG311 uses the SV40 early promoter, while pBG312 uses the adeno-virus-2 major late promoter to drive expression.

We generated plasmid pGAP1.6 which is missing the first intron of the human MIS gene through gapped mutagenesis. The 1600 bp PvuII fragment from chmis 33 was subcloned into the SmaI site of pUC18 to generate pUC18.PV2. This plasmid was linearized with SspI, denatured and then annealed to denatured pUC18. PV2 digested with StuI and MstII. This permitted the formation of hybrid duplexes between the SspI digested and the StuI and MstII digested pUC18. PV2. We then annealed oligomer MIS-42 containing sequence from the 3' end of exon 1 of the human MIS gene and the 5' end of exon 2 of the human MIS gene (i.e., missing the first intron) to the hybrid duplexes.

The sequence of MIS-42 is: 5' TGTTGGCTCC CAGGTCACTT CCTCCAGGTG TAGG 3'. We used DNA polymerase I - large fragment to synthesize the second strand. We then transformed *E. coli* and screened colonies with the $^{32}$P-labeled oligomer. We identified a positive clone, pGAP1.6, and sequenced it to verify that the first intron was deleted. We isolated the 271 bp StuI-MstII fragment for the four way ligation (FIG. 6).

The construction of pMIS D/F in which introns 2, 3, and 4 are deleted involved two steps. In the first step, we isolated a lambda clone λMIS21 from a λgt10 cDNA library made from RNA that was isolated from COS cells transfected with pBG312.hmis (see above). We sequenced the insert of this clone and determined that introns 3 and 4 of the human MIS gene were missing. In the second step, we isolated the 269 bp AvaI - XhoI fragment of MIS21 that spans from exon 3 to the 5' end of exon 5 and ligated it to a linker and the XhoI - HindIII fragment of vector pcHSA35 (described below). The linker was made by synthesizing two oligomers (MIS-56 and MIS-57) of 63 nucleotides containing the DNA sequence from the MstII site in exon 2 to the AvaI site in exon 3, but missing intron 2 of the human MIS gene. In addition, the linker contained DNA sequence encoding a HindIII site at the 5' end (adjacent to the MstII site). The sequence for MIS-56 (top strand) and MIS-57 (bottom strand) is:

```
5' AGCTTCCTGAGGTCACTGTGACGAGGGCTGGGCTGCCGGGTGCCCAGAGCCTCTGCCCCTC 3'
3'     AGGACTCCAGTGACACTGCTCCCGACCGACGGCCCACGGGTCTCGGAGACGGGGAGGGCT 5'.
```

The three way ligation produced plasmid pMIS D/F which is missing introns 2, 3, and 4 of the human MIS gene. The 323 bp MstII - XhoI fragment was then isolated for the four way ligation (FIG. 6).

pcHSA35 is a plasmid constructed from plasmid pcHSA36. pcHSA36 was deposited in the culture collection of the American Type Culture Collection in Rockville, Md. on Dec. 9, 1982 and identified there as HSA-B and assigned ATCC accession number 39253. pcHSA36 was digested with restriction enzyme BstEII to completion, blunt ended with the exonuclease Ba131, followed by digestion with the restriction enzyme BamHI and the sticky ends blunt ended with DNA polymerase I - large fragment. The resulting linear plasmid was circularized by ligation and a plasmid containing a single XhoI site was isolated and designated pcHSA35.

A non-cleavable mutant of MIS is inactive

A mutant protein of MIS was not cleaved with plasmin, and was inactive in the organ culture assay when Arg 427 within the cleavage site was changed to a threonine.

Plasmid pJ103, encoding for a non-cleavable form of human MIS, in which Arg 427 is converted to a threonine, was generated in three steps (FIGS. 7A, 7B, 7C, 7D). Plasmid pJ103 also contains the adenovirus-2 major late promoter driving transcription of the altered MIS cDNA, and a copy of the mouse dihydrofolate reductase (DHFR) cDNA under the control of the SV40 early promoter. These features permit the expression of the altered form of MIS in Chinese hamster ovary (CHO) cells.

Figure 7A:
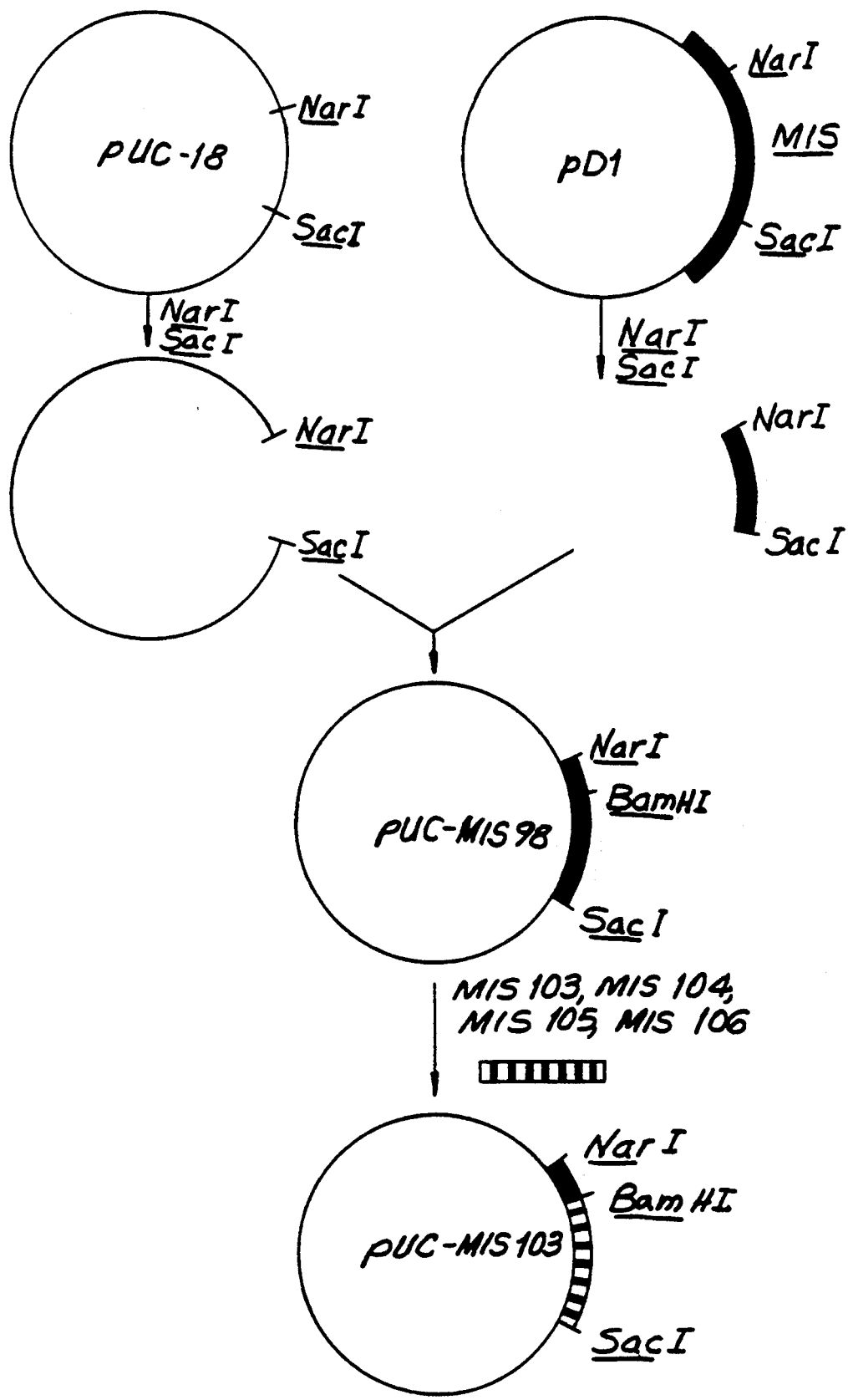

We first inserted oligomers MIS-103, MIS-104, MIS-105, and MIS-106 (FIG. 8) into the BamH1 and Sac1 sites of plasmid pUC-MIS98 to generate pUC-MIS103 (FIG. 7A). Plasmid pUC-MIS98 contains the Nar1-Sac1 fragment of plasmid pD1 in the Nar1 and Sac1 sites of vector pUC-18 (commercially available from International Biotechnologies, Inc., catalog No. 33510 (1986-87)). The construction of pD1 is described above. The nucleotide sequence of plasmid pUC-MIS103 contains a mutation, which changes Arg 427 of human MIS to a threonine.

Figure 7B:
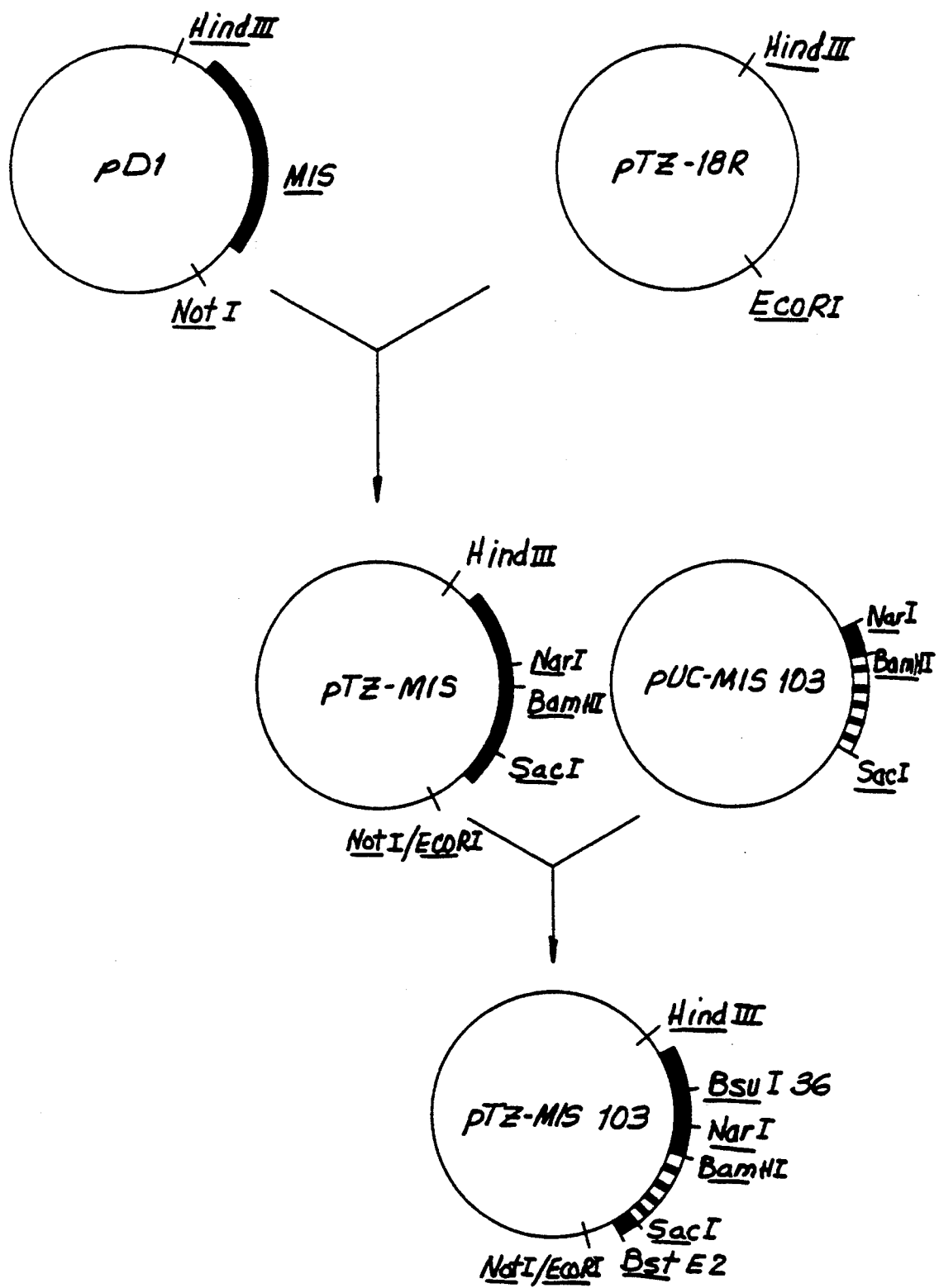
Figure 7C:
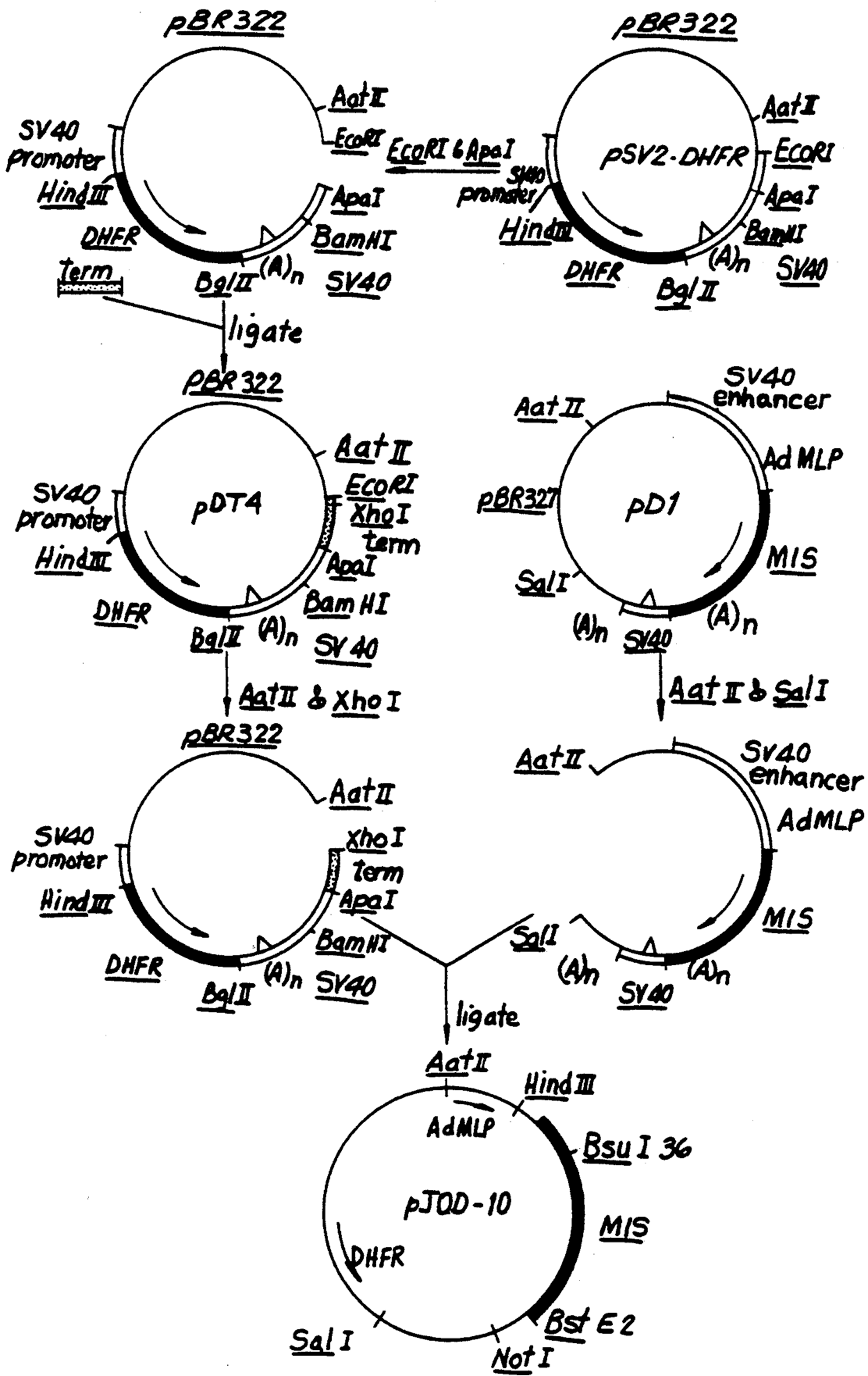

Next, we inserted the Nar1-Sac1 fragment of pUC-MIS103 which contains the mutation into the Nar1 and Sac1 sites of plasmid PTZ-MIS to generate PTZ-MIS103 (FIG. 7B). Plasmid PTZ-MIS contains the Hind3-Not1 fragment of pD1 in the Hind3 and EcoR1 sites of vector pTZ-18R. Prior to the ligations, the Not1 site of the fragment and the EcoR1 site of the vector were converted from 5' overhangs to blunt ends using DNA polymerase I - large fragment and all four deoxynucleotide triphosphates.

Figure 7D:
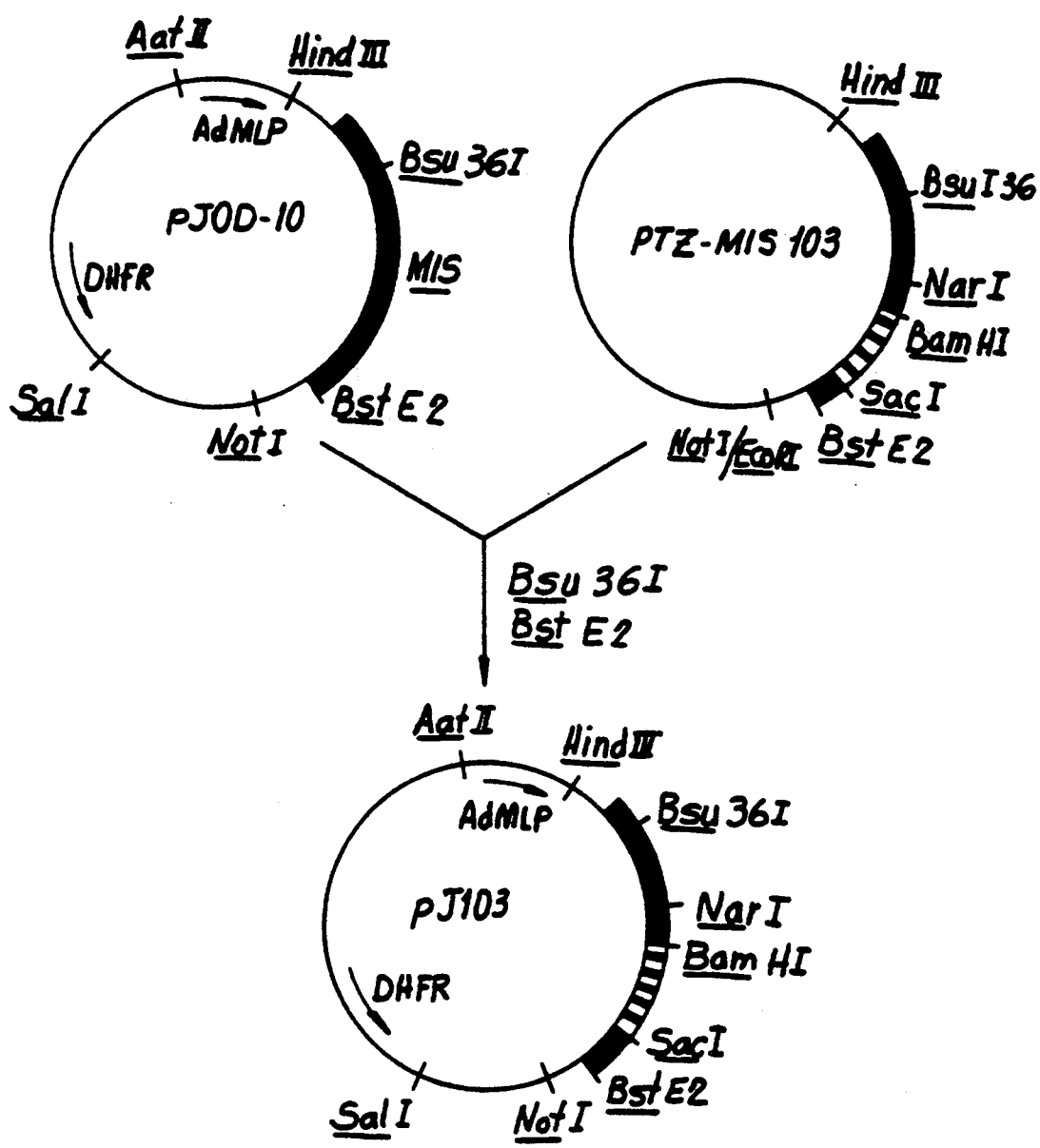

Finally, we inserted the Bsu36 I-BstE2 fragment of plasmid PTZ-MIS103 containing the mutation into the Bsu36 I and BstE2 sites of plasmid PJOD-10 to generate plasmid pJ103 (FIG. 7D).

The vector pJOD-10 (FIG. 7C) contains the human MIS cDNA. The MIS cDNA is expressed from the Adenovirus 2 major late promotor ("AdMLP"), along with the SV40 enhancer. Downstream from the MIS poly A addition site and 3'-genomic flanking sequence are SV40 splice and polyadenylation sites. This vector also contains the murine dihydrofolate reductase ("DHFR") cDNA. The DHFR gene is expressed from the SV40 early promoter and is followed by SV40 splice and polyadenylation signals. The DHFR and MIS cDNA are expressed in opposite orientations. Between the two SV40 poly A sites is a transcriptional termination element. This element was synthesized as an oligonucleotide homologous to the human gastrin gene transcriptional termination sequence (see Sato et al., "A Specific DNA Sequence Controls Termination of Transcription in the Gastrin Gene", Mol. Cell. Biol., 6, pp. 1032-43 (1986)). This terminator element is employed in order to block transcriptional interference between the MIS and DHFR cDNA. The pJOD-10 vector also contains the ampicillin-resistance gene and the ColE1 bacterial origin of replication derived from pBR327, allowing cloning and amplification of this vector in bacteria.

Vector pJOD-10 was constructed (see FIG. 7C) from DNA of three origins: (1) vector PD1 (which comprises the human MIS gene); (2) vector pSV2-DHFR (which comprises the murine DHFR gene); and (3) synthetic oligonucleotide homologous to the human gastrin gene transcriptional terminator. The construction of pD1 is described in Cate et al., European patent application 221,761. The construction of vector pSV2-DHFR is described in Subramani et al., "Expression of the Mouse Dihydrofolate Reductase Complementary Deoxyribonucleic Acid in Simian Virus 40 Vectors", Mol. Cell. Biol., 1(9), pp. 854-864 (1981) and is available from the American Type Culture Collection (ATCC 37146).

Two complementary oligonucleotides homologous to the human gastrin transcriptional terminator were synthesized according to standard procedures using an Applied Biosystems 380A DNA Synthesizer. These oligonucleotides were isolated by gel chromatography. The oligonucleotide corresponding to the gastrin gene coding strand is 51 nucleotides long and comprises a sequence homologous to nucleotides +190 to +233 of the human gastrin gene, according to the map coordinates and sequence of Sato et al., supra. The complementary oligonucleotide is 59 nucleotides long. These oligonucleotides were annealed, forming a double stranded DNA molecule ("term") with an ApaI overhang at one end and an XhoI site and EcoRI overhang at the other end:

```
         +190                                              +233
          |                                                  |
5'      CCTTTTTTTTAATTTTATTTTATTTTATTTTGAGATGGAGTCTCGAGG        3'
3' CCGGGGAAAAAAAATTAAAAATAAAATAAAATAAAAACTCTACCTCAGAGCTCCTTAA 5'.
```

Vector pSV2-DHFR was cut with EcoRI and ApaI and the large fragment was gel purified. The double stranded term insert was then ligated into the ApaI/EcoRI pSV2-DHFR fragment, forming vector pDT4. Vector pDT4 was cut with AatII and XhoI and the large fragment was gel purified. Vector pD1 was cut with SalI and AatII and the large fragment was gel purified. The SalI/AatII pD1 large fragment was inserted into the AatII/XhoI pDT4 large fragment, forming pJOD-10.

Plasmid pJ103 was linearized with the restriction endonuclease PvuI and introduced into CHO DHFR⁻ cells using the calcium phosphate procedure (Scahill, S. J. et al., supra). We selected CHO cell lines expressing the mutant form of MIS in α minimum essential medium without ribonucleosides and deoxyribonucleosides (α-medium), which was supplemented with 10% dialyzed fetal bovine serum (FBS). A cell line (L9C16) expressing in the range of 0.5 mg. of mutant MIS per liter of medium per day was identified using a sandwich ELISA. The cell line was grown in T150 flasks in α-medium containing 5% dialyzed FBS. After the cells were confluent, we replaced the medium every 2-3 days. We then collected 3.3 liters of medium, and clarified by filtration and concentrated to 300 ml using an Amicon concentrator CH2PR with a 30,000 molecular weight cut-off hollow fiber cartridge (H1P30-20). We purified the mutant protein from the concentrate by immunoaffinity chromatography using the M10.6 monoclonal antibody. Mutant MIS was eluted from the affinity matrix with 2M NaSCN, 150 mM NaCl, 15 mM sodium phosphate, pH 6.3. We removed the chaotrope and replaced it with MIS buffer in a P-6DG desalting column (Bio-Rad). 1.2 mg of the mutant protein was recovered, frozen and stored at −70° C.

SDS-PAGE showed that the mutant MIS is a 140 kDa dimer. When the mutant protein was digested with plasmin using the conditions described above, no cleavage was observed (FIG. 9). Using the same conditions as described for FIG. 4, wild type MIS was completely cleaved into the N- and C-terminal dimers.

When we assayed the mutant protein in the organ culture assay, no activity was observed, even at concentrations of 30 μg/ml. In contrast, wild type MIS produces grade 5 regression of the Mullerian duct in the range of 2.5 to 5 μg/ml. Thus we observed that the mutant protein is biologically inactive, and we believe that this lack of activity is a consequence of its inability to be cleaved. Cleavage of the MIS 140k dimer into the N- and C-terminal dimers is, therefore, necessary for biological activity.

Production of the N-terminal dimer

We produced the N-terminal dimer in CHO cells by expressing an altered form of the MIS cDNA in CHO cells.

The plasmid pJ100 encoding the N-terminal domain of human MIS in which the codon for Ser 428 has been converted to a stop codon, was generated in two steps (FIG. 10). This plasmid is similar to pJ103 described above and permits the expression of the N-terminal dimer in CHO cells.

First, we introduced a mutation into plasmid pD1, which contains the human MIS cDNA, using site-specific mutagenesis. The construction of pD1 is described in Cate et al., European patent application 221,761. Two forms of pD1 were made, a linear form using NruI and a gapped form using OxaN1 and BstE2. Both of these forms were heat denatured in the presence of an oligomer MIS-100 which contains the mutation (codon for Ser 428 to stop codon), and annealed to produce a heteroduplex with the MIS-100 oligomer bound to the single strand gap in this heteroduplex. DNA polymerase I - large fragment was used to fill in the single strand regions, and the DNA was used to transform E. coli (DH5). A clone was identified containing a plasmid (pD1-100-1) which contained the mutation. This was verified by restriction enzyme mapping and DNA sequencing.

Next, we inserted the OxaN1-BstE2 fragment of plasmid pD1-100-1 containing the mutation into the OxaN1 and BstE2 sites of plasmid pJOD-10 to generate plasmid pJ100.

Plasmid pJ100 was linearized with Aat2 and introduced into CHO DHFR− cells as described above. A cell line (L7118) expressing the N-terminal dimer of MIS was identified using the sandwich ELISA. Conditioned medium was produced using this cell line and the N-terminal dimer was purified from this conditioned medium as described above.

SDS-PAGE analysis demonstrated that this protein is produced as a dimer, with a slightly larger molecular weight than the N-terminal fragment produced by cleaving full-length MIS with plasmin (FIG. 11). Gel conditions are identical to those used for FIG. 4. Since endoglycosidase F treatment of the N-terminal dimer produced in cell line L7118 and full length MIS produced in cell line L258B9 which contains about 15% cleaved MIS, converts both N-terminal fragments to the same size, it has been concluded that the increase in size of the N-terminal dimer produced in L7118 is due to more glycosylation.

Production of the the C-terminal fragment

A purification of the C-terminal dimer has already been described above using 1M acetic acid to break the non-covalent complex formed after cleaving full-length MIS with plasmin as described above under Purification and Properties of the Carboxyl Terminal Dimer of MIS. Alternatively the C-terminal dimer can be produced using deoxycholate as described above.

Biological activity of the N- and C-terminal dimers

The N- and C-terminal dimers were assayed in the organ culture assay (Donahoe et al., supra.) individually and together. The N-terminal dimer was inactive at a concentration of 40 µg/ml (FIG. 12), while the C-terminal dimer (10 µg/ml) prepared using 1M acetic acid, was also found to be inactive. When the two fragments were assayed together, grade 4 regression of the Mullerian duct was produced (FIG. 12). This result indicates that both fragments are necessary to cause regression of the Mullerian duct, and that both fragments may be necessary to inhibit tumor growth.

The C-terminal dimers prepared using 1% deoxycholate can be assayed individually and together with the N-terminal dimers in the organ culture assay to determine which contains biological activity. A positive result observed using the organ culture assay (Donahoe et al., supra) on the N- and C-terminal dimers individually would indicate that each dimer possesses some distinct biological activity. A positive result observed using the organ culture assay (Donahoe et al. supra) on the N- and C-terminal dimers together would indicate that both fragments together are necessary to produce biological activity. (i.e., both fragments in the same assay, not physically together.) They can also be assayed in primary tumor assays and on cell lines to assess anti-proliferative activity as described in Mosmann, T., "Rapid Colorimetric Assay for Cellular Growth and Survival: Application to Proliferation and Cytotoxicity Assays", *J. Immunol. Methods* 65, 55–63 (1983) and Von Hoff, D. D., B. J. Forseth, M. Huong, J. B. Buchok, B. Lathan, "Improved Plating Efficiencies for Human Tumors Cloned in Capillary Tubes versus Petri Dishes", *Cancer Res.* 64, 4012–4017 (1986).

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A C-terminal dimer of a polypeptide displaying a biological or immunological activity of an MIS protein, said dimer being produced by cleavage between Arg-Ser in the sequence AQRSAG of the polypeptide.

2. The C-terminal dimer according to claim 1, wherein the N-terminal sequence of the monomer of the dimer is SAG.

3. The C-terminal dimer according to claim 1, wherein said dimer is associated with an N-terminal dimer of a polypeptide displaying a biological or immunological activity of an MIS protein by a non-covalent interaction, said N-terminal dimer being produced by cleavage between Arg-Ser in the sequence AQRSAG of the polypeptide.

4. The C-terminal dimer according to claim 3, wherein a monomer of said N-terminal dimer enhances said biological or immunological activity of said C-terminal dimer and has an amino acid formula selected from the formulae:

(a) REEVFSTSALPREQATGSGALIFQQAWDWPLSSLWLP
GSPLDPLCLVTLHGSGNGSRAPLRVVGVLSSYEQAFLEAVRRTHWGL
SDLTTFAVCPAGNGQPVLPHLQRLQAWLGEPGGRWLVVLHLEEVTWE
PTPLLRFQEPPPGGASPPELALLVVYPGPGLEVTVTGAGLPGTQSLC
LTADSDFLALVVDHPEGAWRRPGLALTLRRRGNGALLSTAQLQALLF
GADSRCFTRKTPALLLLLPARSSAPMPAHGRLDLVPFPQPRASPEPE
EAPPSADPFLETLTRLVRALAGPPARASPPRLALDPGALAGFPQGQV
NLSDPAALERLLDGEEPLLLLLPPTAATTGVPATPQGPKSPLWAAGL
ARRVAAELQAVAAELRALPGLPPAAPPLLARLLALCPGNPDSPGGPL
RALLLLKALQGLRAEWRGRERSGSARAQR (b) LRAEEPAVGTSGLIFREDLDWPPGIPQEPLCLVALGG
DSNGSSSPLRVVGALSAYEQAFLGAVQRARWGPRDLATFGVCNTGDR
QAALPSLRRLGAWLRDPGGQRLVVLHLEEVTWEPTPSLRFQEPPPGG
AGPPELALLVLYPGPGPEVTVTRAGLPGAQSLCPSRDTRYLVLAVDR
PAGAWRGSGLALTLQPRGEDSRLSTARLQALLFGDDHRCFTRMTPAL
LLLPRSEPAPLPAHGQLDTVPFPPPRPSAELEESPPSADPFLETLTR
LVRALRVPPARASAPRLALDPDALAGFPQGLVNLSDPAALERLLDGE
EPLLLLLRPTAATTGDPAPLHDPTSAPWATALARRVAAELQAAAAEL
RSLPGLPPATAPLLARLLALCPGGPGGLGDPLRALLLLKALQGLRVE
WRGRDPRGPGRAQR; and (c) portions of the foregoing sequences.

5. A C-terminal dimer of a polypeptide displaying a biological or immunological activity of an MIS protein, the monomer of said dimer having an amino acid formula selected from the formulae:

(a) SAGAAAADGPCALRELSVDLRAERSVLIPETYQANNC QGACGWPQSDRNPRYGNHVVLLLKMQARGATLARPPCCVPTAYTGKL LISLSEERISAHHVPNMVATECGCR or portions thereof displaying said biological or immunological activity; and (b) SAGATAADGPCALRELSVDLRAERSVDLRAERSVLIPEYYQANNC QGVCGWPQSDRNPRYGNHVVLLLKMQARGAALARPPCCVPTAYAGKL LISLSEERISAHHVPNMVATECGCR or portions thereof displaying said biological or immunological activity.

* * * * *

UNITED STATES PATENT AND TRADEMARK OFFICE
CERTIFICATE OF CORRECTION

PATENT NO. : 5,359,033          Page 1 of 3
DATED      : October 25, 1994
INVENTOR(S): Richard L. Cate and R. Blake Pepinsky It is certified that error appears in the above-indentified patent and that said Letters Patent is hereby corrected as shown below:

| Column | Line | |
|---|---|---|
| 1 | 6 | insert a period --.-- after "abandoned" |
| 2 | 23 | insert an --and-- after "MIS105," |
| 3 | 1-2 | change "promotoers" to --promoters-- |
| 3 | 22 | insert a comma --,-- after "ducts" |
| 3 | 22 | delete the "and" |
| 5 | 12 | change the "O" to a --Q-- |
| 8 | 13 | change "E. col" to --E. coli-- |
| 10 | 21 | change "a" to --an-- |
| 10 | 68 | change "pulselabeled" to --pulse-labeled-- |
| 11 | 8 | change "aminoterminal" to --amino-terminal-- |
| 11 | 41 | change "Brillant" to --Brilliant-- |
| 11 | 46 | change "144-48" to --141-48-- |
| 12 | 2 | change "470 A" to --470A-- |

UNITED STATES PATENT AND TRADEMARK OFFICE
CERTIFICATE OF CORRECTION

PATENT NO. : 5,359,033
DATED : October 25, 1994
INVENTOR(S) : Richard L. Cate and R. Blake Pepinsky It is certified that error appears in the above-indentified patent and that said Letters Patent is hereby corrected as shown below:

| Column | Line | |
|---|---|---|
| 12 | 27 | insert a period --.-- after "complex" |
| 13 | 46 | change "in" to --is-- |
| 13 | | delete lines 50-53 |
| 15 | 22 | change "form" to --from-- |
| 15 | 41 | change "pUC18. PV2." to --pUC18.PV2.-- |
| 19 | 32 | change "Carboxyl Terminal" to --Carboxyl-Terminal-- |
| 20 | 6 | insert a comma --,-- after --et al." |

UNITED STATES PATENT AND TRADEMARK OFFICE
CERTIFICATE OF CORRECTION

PATENT NO. : 5,359,033
DATED : October 25, 1994
INVENTOR(S) : Richard L. Cate and R. Blake Pepinsky It is certified that error appears in the above-indentified patent and that said Letters Patent is hereby corrected as shown below:

| Column | Line | |
|--------|------|---|
| 20 | 9 | change the period "." after "activity" to a comma --,-- |
| 22 | 10 | delete the second instance of "DLRAERSV" |

Signed and Sealed this

Twenty-fifth Day of April, 1995

Attest:

BRUCE LEHMAN

Attesting Officer

Commissioner of Patents and Trademarks